Figure 1:
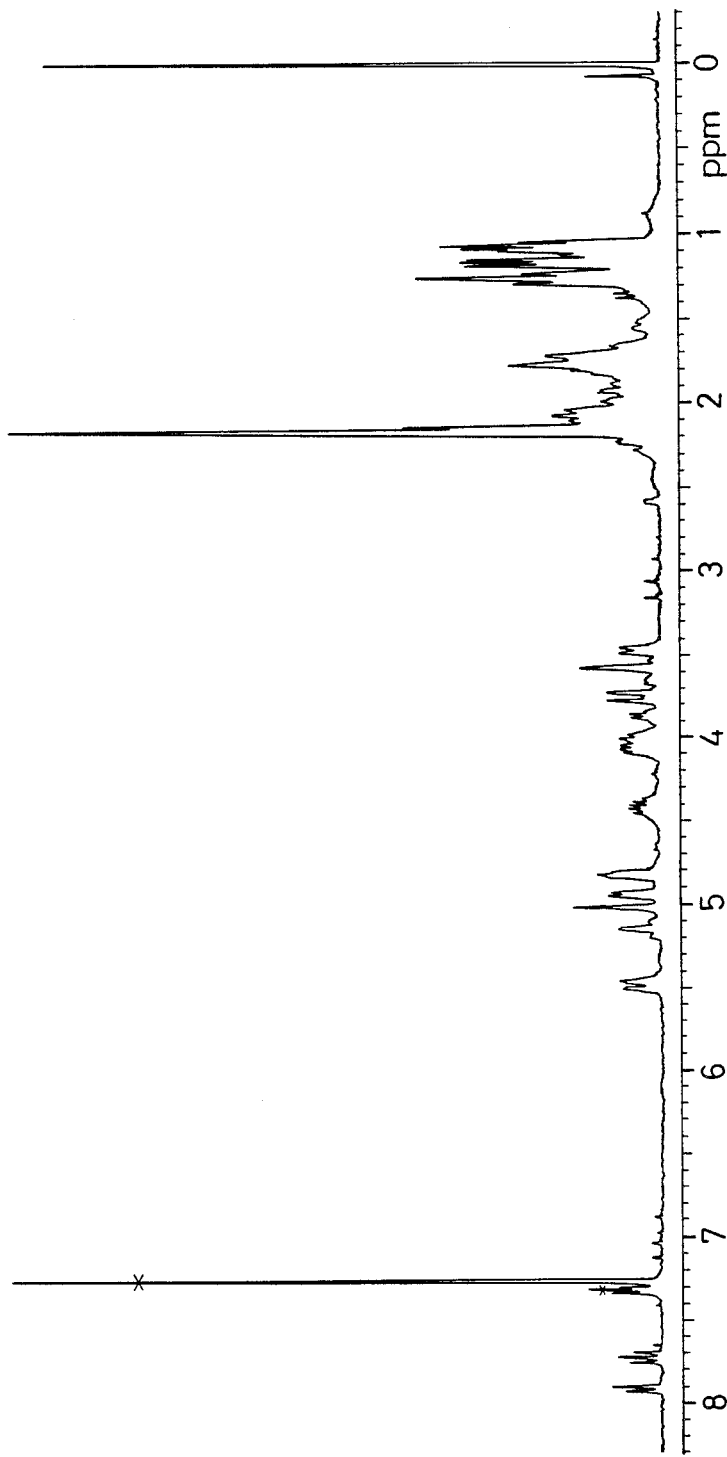

United States Patent [19] [11] Patent Number: 4,713,371
Aretz et al. [45] Date of Patent: Dec. 15, 1987

[54] ANTHRACYCLINE DERIVATIVES AND THEIR USE AS CYTOSTATICS

[75] Inventors: Werner Aretz, Kelkheim; Hans G. Berscheid, Schwalbach; Gerhard Huber, Kelkheim; Hans-Wolfram Fehlhaber, Idstein; Hans P. Kraemer; Hans-Harald Sedlacek, both of Marburg, all of Fed. Rep. of Germany; Bimal N. Ganguli, Bombay, India; Ratan S. Sood, Bombay, India; Julia Gandhi, Bombay, India; Gauknapalli C. Reddy, Bombay, India

[73] Assignee: Hoechst Aktiengesellschaft, Fed. Rep. of Germany

[21] Appl. No.: 824,939

[22] Filed: Feb. 3, 1986

Related U.S. Application Data

[63] Continuation of Ser. No. 624,374, Jun. 25, 1984, abandoned.

[30] Foreign Application Priority Data

Jun. 25, 1983 [DE] Fed. Rep. of Germany ....... 3823025

[51] Int. Cl.$^4$ ....................... A61K 31/71; C07H 15/24
[52] U.S. Cl. ......................................... 514/34; 536/6.4
[58] Field of Search ........................... 514/34; 536/6.4; 260/365

[56] References Cited

U.S. PATENT DOCUMENTS 4,316,011 2/1982 Oki et al. ............................. 536/6.4
4,418,192 11/1983 Tanaka et al. ....................... 536/6.4
4,439,603 3/1984 Umezawa et al. ................... 536/6.4

FOREIGN PATENT DOCUMENTS 0078447 5/1983 European Pat. Off. .

OTHER PUBLICATIONS

Lin et al., J. Med. Chem., 1980, 23, 1242–1244.
Oki et al., The Journal of Antibiotics, vol. XXXIII, No. 11, (Nov. 1980), 1331–1340.
Brockmann et al., Tetrahedron Letters, No. 11, pp. 831–834, (1975).

Primary Examiner—J. R. Brown
Assistant Examiner—Elli Peselev
Attorney, Agent, or Firm—Finnegan, Henderson, Farabow, Garrett & Dunner

[57] ABSTRACT

The present invention relates to the micro-organism Streptomyces purpurascens (DSM 2658), its mutants and variants, a process for the preparation of anthracycline derivatives by fermentation of these cultures and to the anthracycline derivatives themselves. The new compounds are distinguished by antibacterial activity and, in addition, they act against various types of tumors.

12 Claims, 13 Drawing Figures

ANTHRACYCLINE DERIVATIVES AND THEIR USE AS CYTOSTATICS

This application is a continuation of application Ser. No. 624,374, filed June 25, 1984, now abandoned.

The present invention relates to the micro-organism Strepromyces Y-11472 (culture number HPL Y-11472), its mutants and variants and the use of these cultures for the preparation of new antibiotics of the anthracycline type.

The present invention also relates to a process for the preparation of anthracycline compounds by fermentation of Streptomyces Y-11472 or its mutants and variants followed by isolation and purification. Some of these new anthracycline compounds are distinguished by antibacterial action against Gram-positive bacteria and are also active against various types of tumors. The new compounds have the general structure represented in formula I

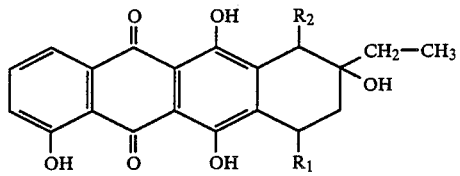

in which $R_1$ denotes H or $OR_3$, and $R_2$ represents $OR_4$ or $COOR_5$, $R_5$ denotes $C_1$-$C_3$-alkyl, and $R_3$ and $R_4$, which can be identical or different, represent hydrogen or sugar combinations of the following composition: Roa—dF—Rod, Roa—dF—Cin A, Roa—dF=Cin B, Roa—Rod—Rod, Roa—dF—Acu, Roa—Rod—Cin A, Roa—Rod—Acu, Rod—Rod—Rod, Roa—Rod or Roa—dF in which Roa denotes rhodosamine, dF denotes deoxyfucose, Rod denotes rhodinose, Acu denotes aculose, Cin A denotes cinerulose A and Cin B denotes cinerulose B, and dF=Cin B denotes that the two sugar units are linked by an extra ether bridge in addition to the usual glycosidic bond.

Streptomyces Y-11472 was isolated in a known manner from a sample of soil, using a nutrient medium at a pH of 6.5 to 8.5, with or without the addition of antibiotics. Streptomyces Y-11472 is preferably isolated from a sample of soil using a nutrient medium at a pH of 6.5-7.0. The antibiotics which, where appropriate, are added to the nutrient medium are preferably ampicillin or amphotericin B. The antibiotics prevent the growth of bacteria and fungi. In addition, streptomycin, penicillin or nystatin can be employed as antibiotics.

The nutrient medium is composed of sources of carbon and nitrogen and of inorganic nutrient salts. Glucose or starch are suitable as the sources of carbon. Peptone, yeast extract, meat extract, malt extract or casein can be used as the sources of nitrogen. Agar can be used to solidify. Examples of suitable inorganic nutrient salts are sodium, potassium, magnesium, calcium, phosphorus or sulphur salts.

The microorganism Streptomyces Y-11472 thus obtained was deposited at the DSM (German Collection of Microorganisms) in D-3400 Göttingen (Grisebachstr. 8) on May 24, 1983, under incoming number DSM 2658.

The microorganism Streptomyces Y-11472 belongs to the order Actinomycetales, to the family of Streptomycetaceae, and to the genus Streptomyces. It is known of various species of Streptomyces which are described in the literature that they produce anthracycline compounds. Daunomycin and adriamycin from these species have already been employed clinically in humans to control cancer.

Rhodomycinones, isorhodomycinones and rhodomycin-related antibiotics are described in Chem. Ber. 88, 1782–1818 (1955); Chem. Ber. 101, 1341–1348 (1968); J. Med. Chem. 20, 957–960 (1977); Pharmacie 27, 782–789 (1972); Zeit. Allg. Mikrobiol., 14, 551–558 (1974); Tetrahed. Lett. No. 38, 3699–3702 (1973); Folia Microbiol., 24, 293–295 (1979); and J. Antibiotics, 32, 420 (1979).

Aclacinomycin A is described in U.S. Pat. No. 3,988,315 and by Oki et al. in J. Antibiotics 28, 830 (1975) and 32, 791–812 (1979).

Cinerubins A and B are described in British Pat. No. 846,130, in U.S. Pat. No. 3,864,480, in "Antimicrobial Agents and Chemotherapy", page 68 (1970) by Keller-Schierlein et al., in Chemical Abstracts 54, 1466i (1960) and in J. Antibiotics 28, 830 (1975).

Other anthracycline antibiotics have been described in detail or summarized in "Index of Antibiotics from Actinomycetes" main editor Hamao Umezawa, University Park Press, State College, Pa., USA (1967) as follows:

| Antibiotic | Page number: |
|---|---|
| Aclacinomycins A and B | 101–102 |
| Adriamycin | 122 |
| Carminomycin I | 225 |
| Galirubins S - D | 405–408 |
| Rhodomycins X - Y | 879–880 |
| β-Rhodomycins | 881–885 |
| γ-Rhodomycins | 886–892 |
| Steffimycin | 945 |

An article by A. Dimarco with the title "Daunomycin and Related Antibiotics" is contained on pages 190–210 of "Antibiotics", Vol. I, Mechanisms of Action, edited by David Gottlieb and Paul D. Shaw, SpringerVerlag New York, Inc., N.Y. (1967).

A report on anthracyclines and their derivatives appears in the "Information Bulletin", No. 10, International Center of Antibiotics, in cooperation with the WHO, December 1972, Belgium.

The properties of Streptomyces Y-11472 are described in Table 2 of this specification.

The present invention also relates to a process for the preparation of compounds of the anthracycline class, of the general formula I, by culturing Streptomyces Y-11472 by fermentation at a pH of 6.5–8.5 and a temperature of 24°–40° C. under aerobic conditions in a nutrient medium containing sources of carbon and nitrogen and inorganic nutrient salts and trace elements, and isolating the compounds from the liquid from the culture and the mycelium in a known manner as described below.

Suitable sources of carbon are glucose, starch, dextrin and glycerol. Suitable sources of nitrogen are soybean meal, yeast extract, meat extract, malt extract, cornsteep liquor, peptone or casein. Examples of suitable inorganic nutrient salts are sodium chloride, magnesium sulfate or calcium carbonate. Iron, magnesium, copper, zinc and cobalt can be used as trace elements.

Streptomyces Y-11472 can be cultured at temperatures of 24°–40° C. at a pH of 6.5–8.5. The culturing of Streptomyces Y-11472 is preferably carried out under aerobic conditions at 30° C. and at a pH of 7.0. After 72 hours, when the highest yield is reached, the fermentation is stopped. It is possible and preferable for the fermentaton to be a submerged fermentation.

The progress of the fermentation and the formation of the anthracycline compounds can be followed using the antibacterial action of the liquid from the culture on *S. aureus* 209 P and *Bac. subtilis*, and by extraction of the entire solution from the culture (mycelium and filtrate from the culture) with an organic solvent and measuring the intensity of absorption of the red compound at 494 nm. Ethyl acetate is preferably used as the organic solvent.

The anthracycline compounds in the filtrate from the culture and in the mycelium are isolated in accordance with the scheme shown in Diagram I of the present invention.

The anthracycline compounds in the mycelium are extracted with an organic solvent, preferably with aqueous acetone, which has been adjusted to a pH of 3.5. After removing the acetone, the pH of the aqueous phase is adjusted to 7.5 and it is then extracted with ethyl acetate. The liquid from the culture is extracted at a pH of 7.5 with an organic solvent, such as ethyl acetate or chloroform, preferably with ethyl acetate. The ethyl acetate extracts from the mycelium and the filtrate from the culture are worked up together or separately, concentrated and taken up in an organic solvent, such as benzene or toluene. Toluene is preferably used. The toluene solution is then extracted with an acetate buffer at a pH of 3.5. The mixture of anthracycline derivatives is divided into two fractions at this stage. The mixture remaining in the toluene phase is denoted fraction A, and the mixture of glycosides remaining in the aqueous phase is denoted fraction B.

Fraction A is further purified as illustrated in Diagram II of the present invention. Fraction B is further purified in accordance with Diagram III of the present invention.

As can be seen from Diagram II, at least four components derive from fraction A, and of these components cytorhodin J is enriched and finally isolated in a pure form by multistage chromatography.

As illustrated in Diagram III, from fraction B are isolated the cytorhodins A, B, C, D, E, F, the mixture G+I (1:1), H, K, L, M, the mixture N+O, P, V and W. The fractions "X" and "Y" are mixtures of anthracycline compounds some of which are still under investigation. Their general structure corresponds to formula I.

The compounds isolated from the solution from the culture of Streptomyces Y-11472 and purified in accordance with Diagram I have the general formula I.

Some of the compounds according to the invention have the structure represented in formula II

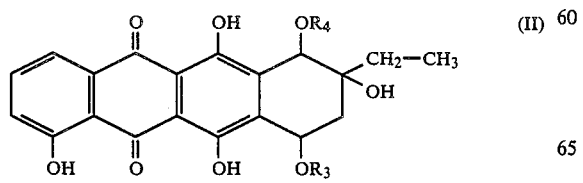

in which $R_3$ and $R_4$ have the above meaning.

Diagram I

Isolation of the antibiotic complex from Streptomyces Y-11472

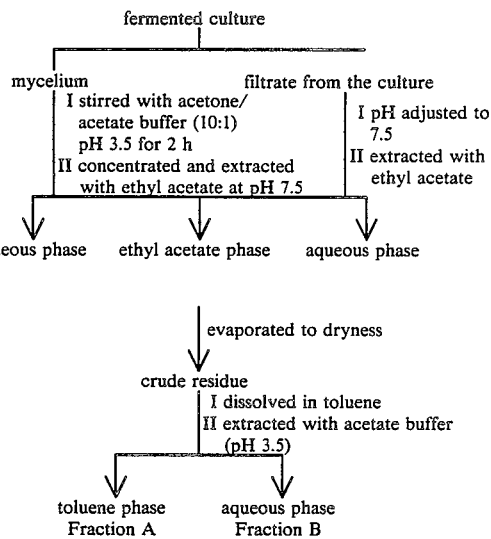

Diagram II

Purification of Fraction A

Crude fraction A: 5 g
|
silica gel column 2.8 × 68 cm, 175 g
eluted with 2% methanol in CHCl$_3$

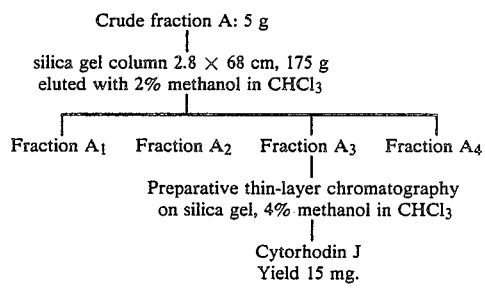

Preparative thin-layer chromatography
on silica gel, 4% methanol in CHCl$_3$
|
Cytorhodin J
Yield 15 mg.

Diagram III

Work-up of aqueous phase B

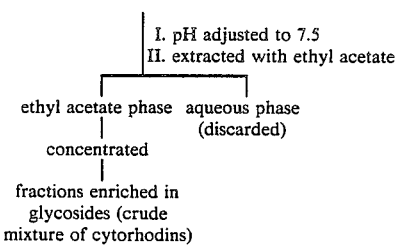

-continued
Diagram III
Work-up of aqueous phase B

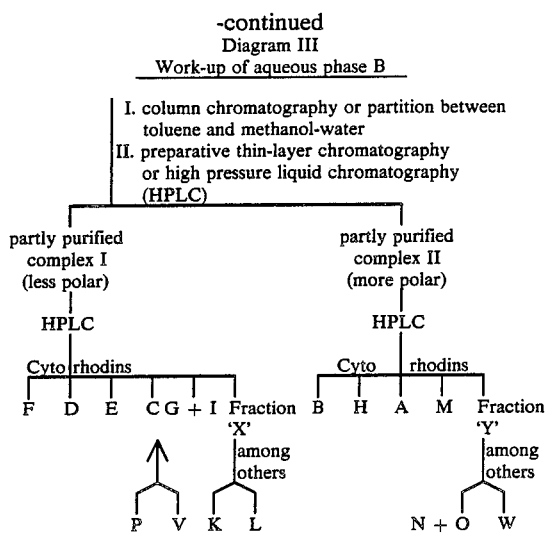

Other compounds according to the invention have the structure represented in formula III

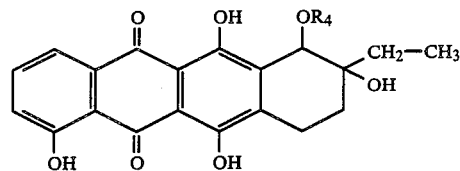

in which R₄ has the meaning mentioned above, or the structure represented in formula IV

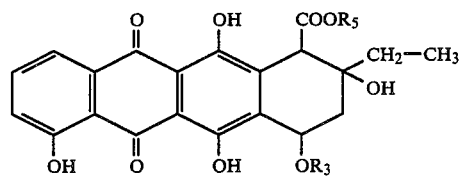

in which $R_3$ and $R_5$ have the meaning mentioned above.

Particularly preferred compounds according to the invention are those of the formula II

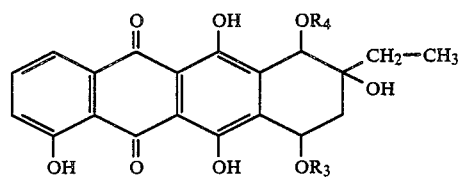

in which $R_3$ and $R_4$ have the meanings indicated below:

| Compound | R₃ | R₄ |
| --- | --- | --- |
| Cytorhodin F | Roa-Rod-Acu (formula V) | Roa-Rod-Acu (formula V) |
| Cytorhodin D | Roa-dF = Cin B (formula VI) | Roa-Rod-Acu (formula V) |
| Cytorhodin C | Roa-dF = Cin B (formula VI) | Roa-dF = Cin B (formula VI) |
| Cytorhodin B | Roa-dF-Cin A (formula VII) | Roa-Rod-Rod (formula VIII) |
| Cytorhodin A | Roa-Rod-Rod (formula VIII) | Roa-Rod-Rod (formula VIII) |
| Cytorhodin G | Roa-df = Cin B (formula VI) | Roa-dF-Cin A (formula VII) |
| Cytorhodin I | Roa-dF-Cin A (formula VII) | Roa-dF = Cin B (formula VI) |
| Cytorhodin P | Roa-dF-Cin A (formula VII) | Roa-Rod-Acu (formula V) |
| Cytorhodin V | Roa-Rod-Acu (formula V) | Roa-Rod-Rod (formula V) |
| Cytorhodin N | Roa-Rod-Rod (formula VIII) | Roa-dF-Rod (formula X) |
| Cytorhodin O | Roa-dF-Rod (formula X) | Roa-Rod-Rod (formula VIII) |
| Cytorhodin W | Roa-dF-Rod (formula X) | Roa-dF-Rod (formula X) |

Other particularly preferred compounds are cytorhodin E, K, L and M of the general formula III

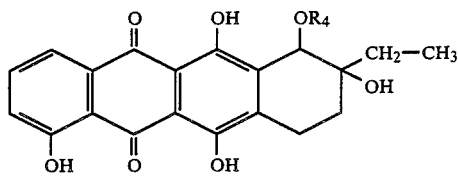

in which R₄ has the meanings indicated below:

| Compound | R₄ |
| --- | --- |
| Cytorhodin E | Roa-Rod-Rod (formula VIII) |
| Cytorhodin K | Roa-dF-Rod (formula X) |
| Cytorhodin L | Roa-Rod (formula XII) |
| Cytorhodin M | Roa-dF (formula XIII) | and cytorhodin J of the general formula IV

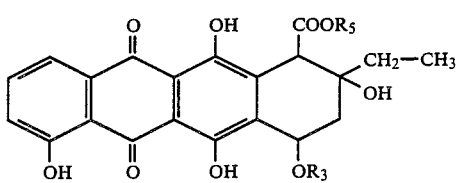

in which $R_5$ denotes methyl, and $R_3$ denotes the sugar combination Rod—Rod—Rod (formula IX). The abovementioned sugar combinations have the following structural formulae (V to IX):

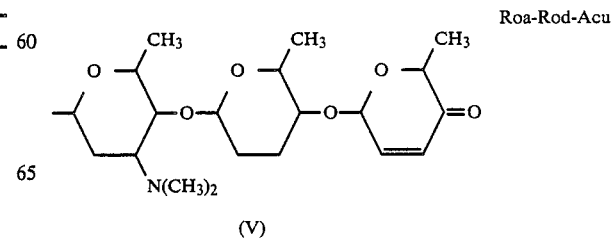

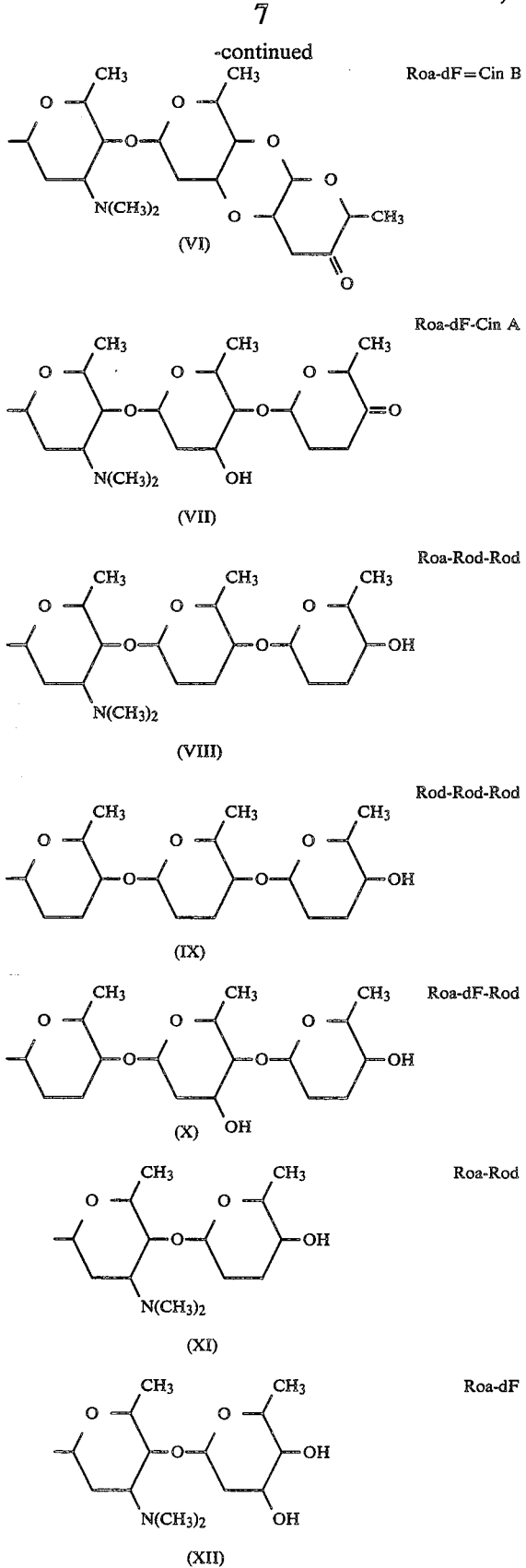

The anthracycline compounds according to the invention are distinguished by a potent action on Gram-positive bacteria and a pronounced cytostatic action.

The present invention is illustrated in detail by the examples which follow:

EXAMPLE 1

Isolation of Streptomyces Y-11472 from soil (a) Preparation of the nutrient media for isolation

| | | |
|---|---|---|
| Medium 1: | Glucose | 1.0 g |
| | Glycerol | 1.0 g |
| | L-Arginine | 0.3 g |
| | $K_2HPO_4$ | 0.3 g |
| | $MgSO_4 \cdot 7H_2O$ | 0.2 g |
| | NaCl | 0.3 g |
| | Yeast extract | 2.0 g |
| | $Fe_2(SO_4)_3$ | 10 mg |
| | $CuSO_4 \cdot 5H_2O$ | 1 mg |
| | $ZnSO_4 \cdot 7H_2O$ | 1 mg |
| | $MnSO_4 \cdot 7H_2O$ | 1 mg |
| | Agar | 15 g |
| | Distilled water | 1 l |
| | pH | 6.5 |
| Medium 2: | Glucose | 2.0 g |
| | L-Asparagine | 1.0 g |
| | $K_2HPO_4$ | 0.5 g |
| | $MgSO_4 \cdot 7H_2O$ | 0.5 g |
| | Soil extract | 200 ml |
| | Agar | 15 g |
| | Distilled water | 800 ml |
| | pH | 8.0 |
| Medium 3: | Starch | 10.0 g |
| | Casein | 0.3 g |
| | $KNO_3$ | 2.0 g |
| | NaCl | 2.0 g |
| | $K_2HPO_4$ | 2.0 g |
| | $MgSO_4$ | 0.05 g |
| | $CaCO_3$ | 0.02 g |
| | $FeSO_4$ | 0.01 g |
| | Agar | 15 g |
| | Distilled water | 1 l |
| | pH | 7.2–7.5 |

The media were sterilized at 121° C. for ½ hour.

(b) Preparation of a suspension of a soil sample 1 gram of soil sample was dried in air, crushed in a mortar and heated at 120° C. for 1 hour. The soil sample thus treated was suspended in distilled water and thoroughly shaken. The earth was then allowed to sediment and the supernatant liquid was used as the inoculum for the above media for isolation.

(c) Inoculation of the media for isolation 1 ml of suspension of soil sample was inoculated onto Petri dishes each containing 50 ml of the above media for isolation.

(d) Isolation of Streptomyces Y-11472

The inoculated Petri dishes were incubated at 37° C. for 2 weeks, and Streptomyces Y-11472 was isolated in a known manner from the growing microorganisms.

EXAMPLE 2

Culturing Streptomyces Y-11472 for the fermentative production of the antibiotic complex Streptomyces Y-11472 was added to yeast-malt agar of the following composition:

| | |
|---|---|
| malt extract | 10.0 g |
| yeast extract | 4.0 g |
| glucose | 4.0 g |
| agar | 15.0 g |
| distilled water | 1 liter |
| pH | 7.0 |

The medium was distributed into test tubes and sterilized at 121° C. for 30 min, then the tubes were cooled at a slant to produce slant cultures, inoculated with the culture and incubated at 28° C. for 10–15 days. At the end of this time, good growth and good spore formation were found. A suspension of spores in distilled water from a slant tube was used as the inoculum for 5 conical flasks each containing 100 ml of inoculum medium or for 1 5-liter suction flask containing 1 liter of the same stock culture medium.

Composition of the seed culture medium

| | |
|---|---|
| Glucose | 15.0 g |
| Soybean meal | 15.0 g |
| Cornsteep liquor | 5.0 g |
| CaCO$_3$ | 2.0 g |
| NaCl | 5.0 g |
| Distilled water | 1 liter |
| pH | 7.0 |

100 ml of the above medium was placed in each of a number of 500 ml conical flasks, or 1 liter of the medium was poured into a 5-liter suction flask, and the medium was sterilized at 121° C. for 30 minutes. The flasks were cooled, inoculated with the suspension of spores and shaken at 240 rpm and 30° C. for 72 hours in a rotating shaking machine with an excursion of 3.75 cm. The grown culture was used as the inoculum for a 15-liter glass fermenter containing 10 liters of a 5% by volume stock culture medium in order to prepare an inoculum for the 2nd stage. The fermentation was carried out at 26° C. (±1° C.), stirring at 160–180 rpm, with an aeration rate of 6–7 liters/min. The well grown inoculum thereby obtained was used as the inoculum for the production medium.

Composition of the production medium

| | |
|---|---|
| Glucose | 20.0 g |
| Malt extract | 10.0 g |
| Yeast extract | 4.0 g |
| Distilled water | 1 liter |
| pH | 6.8 |

0.025% of Desmophen ® was added as an antifoam agent to the batches in the fermenter.

260 liters of the above medium were placed in a 390-liter fermenter. The medium was sterilized indirectly and directly by steam at 121° C. for 28 min. The fermenter was cooled and inoculated with the inoculum from the 2nd stage (5% by volume). Fermentation was carried out at 26° C. (±1° C.) for 68–72 hours, stirring at 100–200 rpm, at an aeration rate of 1:0.6 VVM (9–10 m$^3$/h). On stopping fermentation after 68–72 hours, the concentration of the antibiotic was 100–150 µg per ml, and the pH of the liquid from the culture was 5.5–6.0. The residual sugar content in the solution from the culture was 0.03–0.5%, and the wet weight of the mycelium was 3–4 g/Vol.-%.

EXAMPLE 3

Culture of Streptomyces Y-11472 for the fermentative preparation of the antibiotic complex

| | | |
|---|---|---|
| (a) (1) Composition of the seed culture medium | | |
| | Gram seed powder | 10.0 g |
| | Dextrose | 10.0 g |
| | NaCl | 5.0 g |
| | CaCO$_3$ | 3.0 g |
| | Distilled water | 1 l |
| | pH | 7.0 |
| | 72 hours at 30° C. | |
| (2) Composition of the production medium | | |
| | Starch | 10.0 g |
| | Glucose | 10.0 g |
| | Malt extract | 7.5 g |
| | Peptone | 7.5 g |
| | NaCl | 3.0 g |
| | MgSO$_4$ | 1.0 g |
| | KH$_2$PO$_4$ | 2.0 g |
| | CuSO$_4$.5H$_2$O | 0.007 |
| | FeSO$_4$.7H$_2$O | 0.001 |
| | MnSO$_4$.4H$_2$O | 0.008 |
| | ZnSO$_4$.7H$_2$O | 0.002 |
| | Distilled water | 1 l |
| | pH | 7.0 |
| | Duration of fermentation: 88–96 hours. | |
| (b) (1) Composition of the seed culture medium | | |
| | Malt extract | 10.0 g |
| | Yeast extract | 4.0 g |
| | Glucose | 4.0 g |
| | Distilled water | 1 l |
| | pH | 7.0 |
| | 72 hours at 30° C. | |
| (2) Composition of the production medium | | |
| | Starch | 10.0 g |
| | Glucose | 10.0 g |
| | Soybean meal | 15.0 g |
| | K$_2$HPO$_4$ | 1.0 g |
| | MgSO$_4$ | 1.0 g |
| | NaCl | 3.0 g |
| | CuSO$_4$.5H$_2$O | 0.007 g |
| | FeSO$_4$.7H$_2$O | 0.001 g |
| | MnCl$_2$.4H$_2$O | 0.008 g |
| | ZnSO$_4$.7H$_2$O | 0.002 g |
| | Distilled water | 1 l |
| | pH | 7.0 |
| | Harvesting after 88–96 hours. | |

EXAMPLE 4

Isolation of the crude mixture of anthracycline compounds

About 250 liters of the culture from a 300-liter fermenter were centrifuged.

(a) 200 liters of filtrate from the culture were adjusted to pH 7.5 with NaOH and extracted twice with 50 liters of ethyl acetate each time, then the organic phase was concentrated in vacuo. The aqueous phase which separated out during this was removed and extracted 3 times with ethyl acetate. The combined organic phases were evaporated to dryness in vacuo, the residue was dissolved in 650 ml of toluene and the solution was extracted 5 times with 300 ml of sodium acetate buffer pH 3.5 each time, and the toluene phase was evaporated in vacuo (red oily residue, fraction A). The combined aqueous phases were adjusted to pH 7.5 with 2N NaOH, and extracted 4 times with 400 ml of ethyl acetate. The removed ethyl acetate phases were evaporated to dryness in vacuo (0.7 g of deep red solid residue: fraction B).

(b) 9.5 kg of solid mycelium were extracted twice with 50 liters of acetone/acetate buffer pH 3.5 (10:1) each time, the combined extracts were concentrated to 12 liters in vacuo (pH 3.5), the concentrate was washed 3 times with 4 liters of toluene, and the toluene phases were combined and concentrated in vacuo to an oily deep red residue. The aqueous phase was adjusted to pH 7.5 with concentrated NaOH, extracted 3 times with 4 liters of ethyl acetate each time, and the combined ethyl acetate phases were evaporated in vacuo. 1.98 g of a deep red solid residue (fraction B) remained.

(c) The process of further isolation is clear from Diagrams I to III. For example, the compound cytorhodin J was obtained by preparative thin-layer chromatography of the partly purified fraction $A_3$ obtained from column chromatography (Diagram II).

Cytorhodines A, B, C, E, F, H, K, L, M, P, V and W and the 1:1 mixtures of G+I and N+O were isolated by partitition between toluene and methanol-water or repeated chromatography of the fractions enriched in glycosides (Diagram III) on silica gel or on "reverse phase" adsorbents or DCCC (droplet counter current chromatography). The last stage in the purification was carried out by preparative thin-layer and high pressure liquid chromatography (HPLC). HPLC was carried out using a column containing Microporasil ® (Waters) or Lichrosorb ® Si 60 (Merck) and a mobile phase of the following composition: chloroform:methanol:acetic acid:water:triethylamine in the ratio 68:20:10:2:0.01. The flow rate was set at 0.5–1.5 ml per minute and detection was carried out by UV absorption at 254, 260 or 490 nm in a flow photometer.

EXAMPLE 5

Identification of cytorhodin J (formula IV with $R_3$=Rod—Rod—Rod and $R_5$=$CH_3$)

15 mg were isolated as indicated in Diagram II. Melting point: 128°–130° C.

Absorption spectrum (methanol): 242, 284, 492, 510, 522 and 558 nm.

$^1$H-NMR

δ values (ppm):
1.1–1.22 (12H, m, 4×$CH_3$)
1.75–2.25 (14H, m, 7×—$CH_2$—)
2.36 (2H, m, —$CH_2$—)
3.51 to 3.6 (3H, m, 4', 4'', 4'''—H) 3.7 (3H, s, —$COOCH_3$)
3.94–4.12 (3H, m, 5', 5'', 5'''—H)
4.3 (1H, s, C10—H)
4.83–4.86 (2H, m, 1'', 1'''—H)
5.28 (1H, br, C7—H)
5.45 (1H, br, c1'—H)
7.34 (1H, d, J=8 Hz, C1H)

EXAMPLE 6

Isolation of the compounds cytorhodin A, B and H as a crude mixture 1.0 g of a crude mixture of cytorhodins, obtained by extraction out of the solution from the culture as described in Diagram I, was chromatographed on 100 g of 31μ silica gel (Grace) in a 3×43 cm glass column using the mixture $CHCl_3$/methanol/96% strength acetic acid/water/Triethylamine 80:5:5:1:0.01 ("System B"). The sample was dissolved in 7 ml of the mobile phase, applied to the equilibrated column, and 23 ml fractions were collected and assessed by thin-layer chromatography (on pre-coated TLC plates or sheets silica gel 60 F 254 (Merck) with the mixture $CHCl_3$/methanol 96% strength acetic acid/water/triethylamine 80:10:10:2:0,01 ("system B"):

| 1-139 | 238 mg | Mixture of compounds C, D, E, F and G + I |
| 140-220 | 189 mg | Mixture of compounds A, B, H, M |
| 221-288 | 138 mg | Mixture of polar products (fraction "Y") |

Further column chromatographies were carried out with the crude mixture of cytorhodine products in an analogous manner. Mixed fractions having the same composition were further separated by HPLC in steel columns.

EXAMPLE 7

Isolation of the individual components cytorhodin A, B and H by high pressure liquid chromatagraphy (HPLC)

52.5 mg of a mixed fraction containing cytorhodin A, B and H were dissolved in 2 ml of the system B (Ex. 6) and applied to a steel column (2.1×25 cm) which had been filled under pressure with 40 g of 7μ Li-Chrosorb ® S160 Merck, and equilibrated with the above mobile phase. Elution was carried out at a flow rate of 5 ml/min and was followed with a flow spectrophotometer at a wavelength of 490 nm, 4 ml fractions being collected and combined after checking by analytical HPLC:

| Fraction | | Compounds | $R_F$ in system B |
|---|---|---|---|
| 19–22 | 6 mg | Cytorhodin B | 0.33 |
| 23–27 | 7 mg | Mixed fraction Cytorhodin B + H + A | 0.3 |
| 28–37 | 15 mg | Cytorhodin A | 0.27 |

To isolate the compound cytorhodin H, the mixed fractions from several runs were rechromatographed in the same manner.

The pure individual components from several chromatographic runs were combined and again purified by the process which follows.

120 mg of combined batches of cytorhodin A isolated by repeated column chromatography as described were dissolved in 30 ml of sodium acetate buffer pH 3.5, the solution was adjusted to pH 7.8 with 2N NaOH and was extracted 4 times with 15 ml of ethyl acetate each time, and the combined organic phases were washed once with 1 ml of a 0.001 molar solution of EDTA (pH 7.5) and then twice with 2 ml of water each time, dried over $Na_2SO_4$, filtered and evaporated in vacuo. The residue was dissolved in a little $CHCl_3$, and the solution was filtered under suction through a glass frit and, after adding heptane, was evaporated in vacuo until opalescent.

Figure 2:
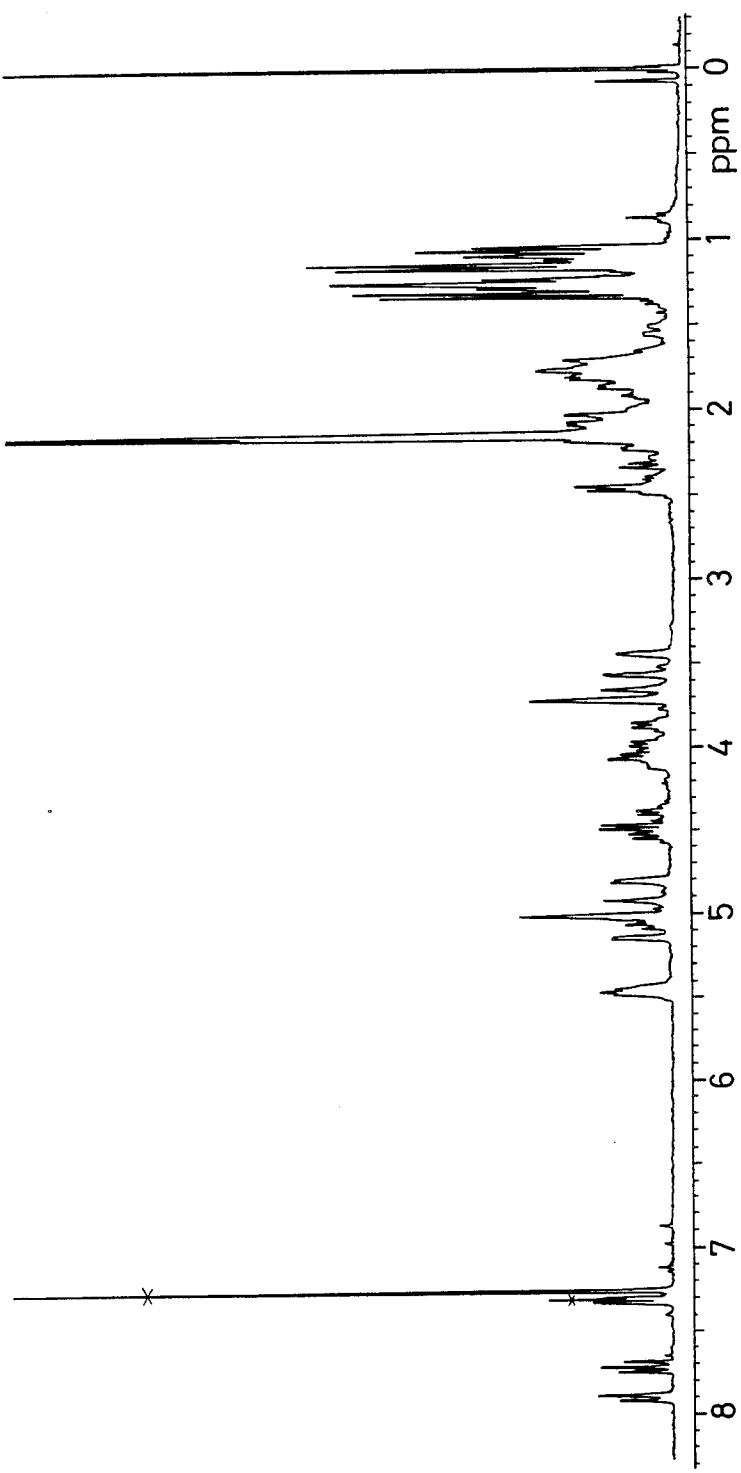
Figure 3:
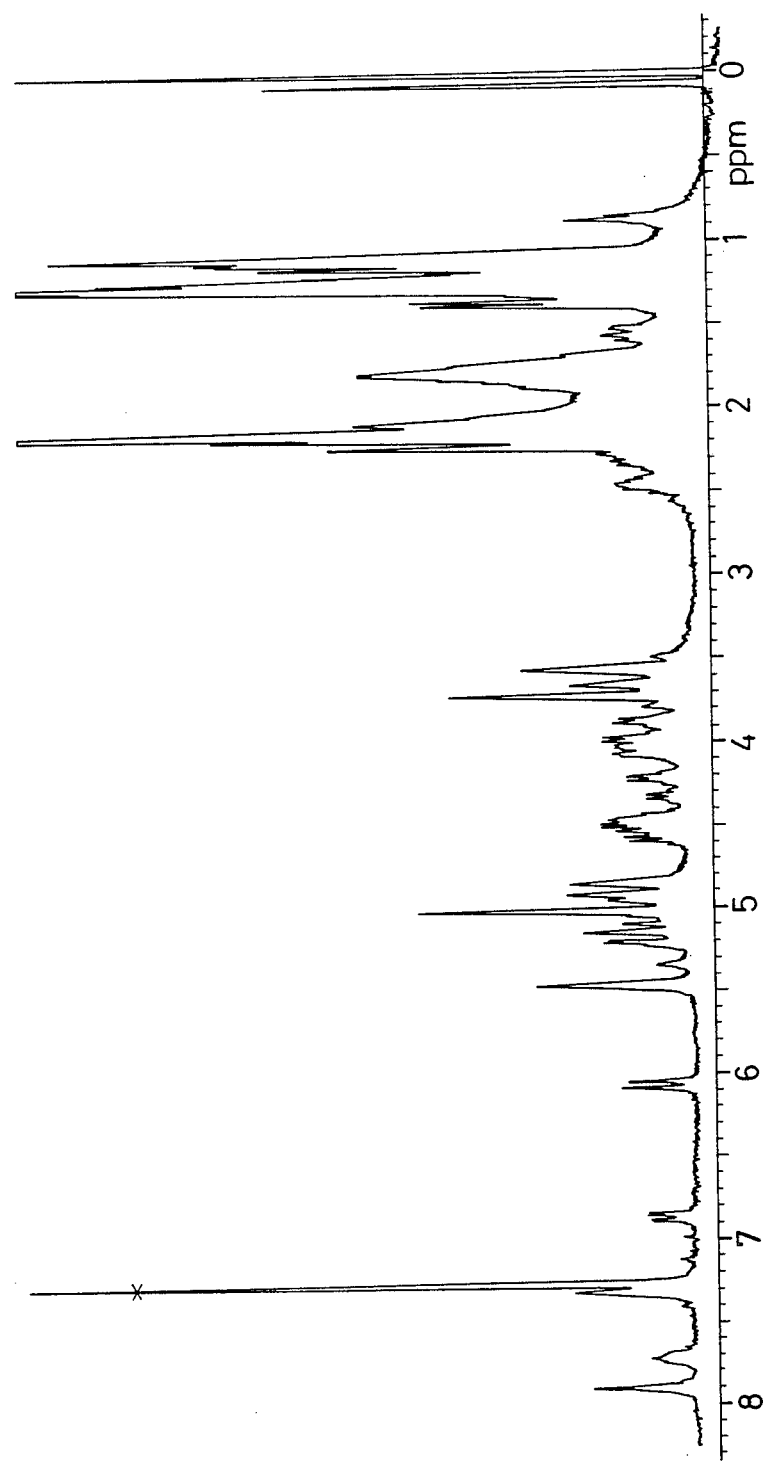

| A: $^1$H—NMR | | | FIG. 1 |
|---|---|---|---|
| Absorption spectrum | (a) 235 (4.62) | 253 (Sh) | 295 (3.87) 4.95 (4.11) |
| | (b) 235 (4.62) | 255 (Sh) | 296 (3.92) 4.97 (4.17) |
| | (c) 243 (4.63) | — | 280 (3.95), 305 (3.91), 575 and 610 (4.15) |
| $C_{60}H_{88}N_2O_{20}$, MW calc.: 1156 (confirmed by FAB-MS) | | | |
| B: $^1$H—NMR | | | FIG. 2 |
| Absorption spectrum | (a) 235 (4.52) | 252 (Sh) | 297 (3.83) 4.95 (3.94) |
| | (b) 236 (4.52) | 253 (Sh) | 295 (3.89) 4.95 (4.03) |
| | (c) 242 (4.40) | — | 280 (3.89), 305 (3.69), 610 (3.83) |
| $C_{60}H_{86}N_2 _{21}$, MW calc.: 1170 (confirmed by FAB-MS) | | | |
| H: $^1$H—NMR | | | FIG. 3 |
| Molecular weight MW 1150–1300 (FAB-MS) | | | |

EXAMPLE 8

Isolation of cytorhodin E by preparative high pressure liquid chromatography (HPLC)

30 mg of crude cytorhodin were dissolved in 0.5 ml of a mixture of $CHCl_3$/methanol/96% acetic acid/water/triethylamine 400:25:50:5:0.05 and applied to a 2.5×30 cm steel column packed with about 40 g of silica gel 7μ Lichrosorb ® 60 (Merck), and chromatographed under pressure with the above mixture at a flow rate of 6 ml/min. After a forerun of 100 ml, the fractions recognizable using a flow detector at the wavelength 260 nm were, after checking by analytical HPLC, combined.

| Fractions | Compounds | $R_F$ in system A |
|---|---|---|
| 43–48 | Cytorhodin F | 0.63 |
| 49–51 | Cytorhodin D + E | 0.53 |
| 52–62 | Cytorhodin E | 0.53 |
| 110–135 | Cytorhodin C | 0.44 |

The fractions of the same composition obtained from six preparative HPLC runs carried out in the same manner were, after checking by analytical HPLC, combined, each dissolved in 20 ml of aqueous Na acetate buffer pH 3.5, and 1 ml of 0.001 molar aqueous ethylenediaminetetraacetic acid solution (EDTA; adjusted to pH 3.5 with NaOH) was added and the mixture was shaken with 5 ml of toluene. The toluene phase was discarded, and the aqueous phase was adjusted to pH 7.5 with 2N NaOH and extracted with 20 ml of $CHCl_3$. After drying over sodium sulfate, the mixture was filtered and the filtrate was evaporated in vacuo. The following were obtained:

| Compounds | | $R_F$ in system A |
|---|---|---|
| Cytorhodin F | 8 mg | 0.63 |
| D + E | 10 mg | 0.53 |
| E | 21 mg | 0.53 |
| C | 21 mg | 0.44 |

Analytical HPLC was carried out with the above mobile phase on a ready-packed 7μ Lichrosorb ® Si 60 (Merck) 4×125 mm column. Detection was at 260 nm using a spectrophotometer with a flow cell.

Figure 4:
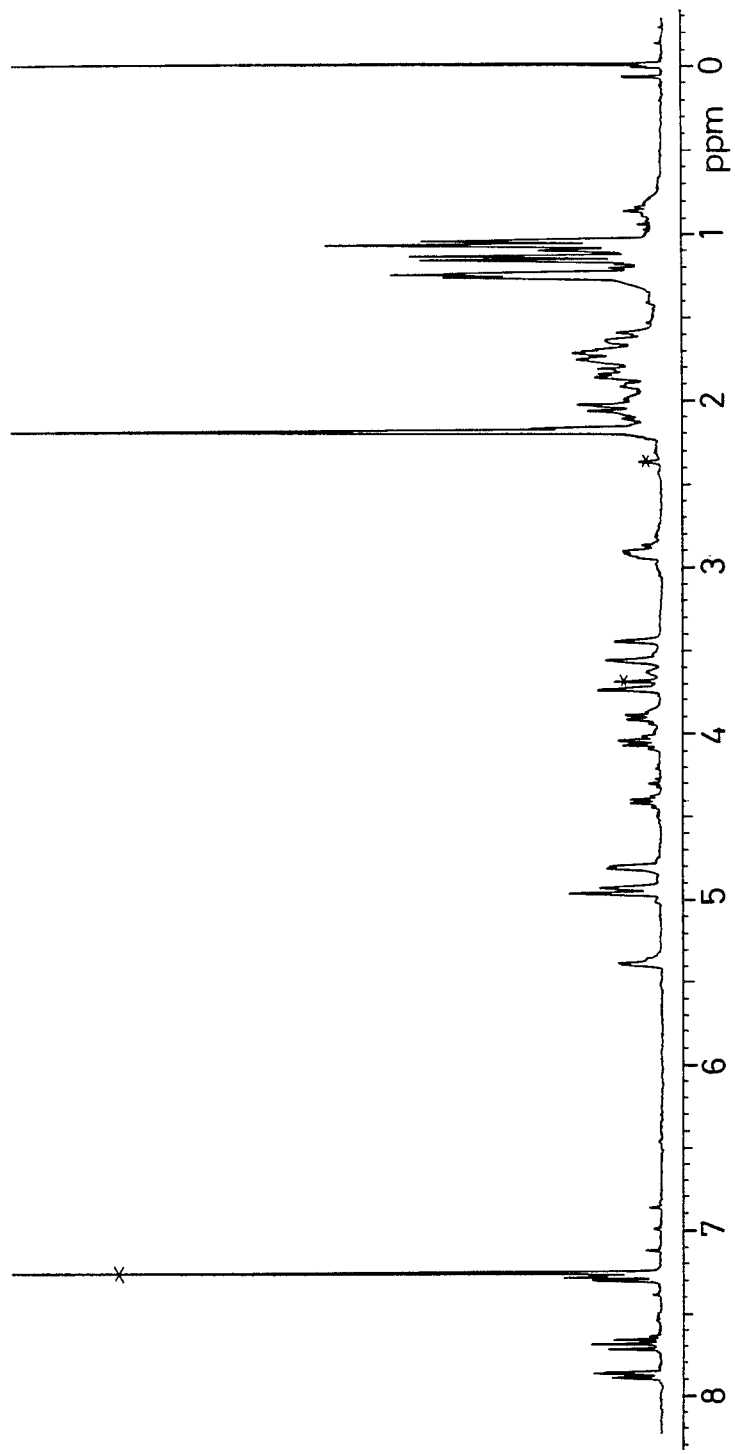

E: $^1$H—NMR Absorption spectrum  FIG. 4

| (a) 235 (4.57) | 253 (Sh) | 295 (3.85) | 495 (4.1) |
|---|---|---|---|
| (b) 236 (4.58) | 256 (Sh) | 296 (3.9) | 498 (4.15) |
| (c) 243 (4.6) | — | 305 (3.88) | 610 (4.1) |

$C_{40}H_{53}N_1O_{13}$, MW calc. 755 (confirmed by FAB-MS)

EXAMPLE 9

Isolation of cytorhodin F, D, C and G+I 2 g of crude cytorhodin were dissolved in 50 ml of a mixture of chloroform/methanol/glacial acetic acid water 80:10:10:2 (system A) and applied to a 2.75×42 cm column containing 15–40μ silica gel 60 "Merck" slurried in system A. The eluting agent used was system A containing 0.01% of Na heptanesulfonate. After a forerun of 1.1 liters, 25 ml fractions were collected and checked by analytical TLC (system A). The active components were eluted in the following fractions:

| | Cytorhodin | | $R_F$ in system A |
|---|---|---|---|
| 40–44 | F | 20 mg | 0.63 |
| 45–49 | F + D | 60 mg | |
| 50–76 | D | 263 mg | 0.53 |
| 77–93 | D + C | 145 mg | |
| 94–126 | C | 260 mg | 0.44 |
| 127–153 | C + P + V + G + I | 135 mg | |
| 154–192 | G + I | 175 mg | 0.34 |

Treating the column with methanol lead to elution of mixtures of more polar components, fraction "X", mainly.

A saturated aqueous solution of $Na_2HPO_4$ was added to the combined fractions until the chloroform phase separated out, and the chloroform phase was washed with one volume each of 5% strength $Na_2HPO_4$ solution and then of water, dried over anhydrous sodium sulfate, concentrated in vacuo and the product was precipitated with petroleum ether or hexane.

Figure 5:
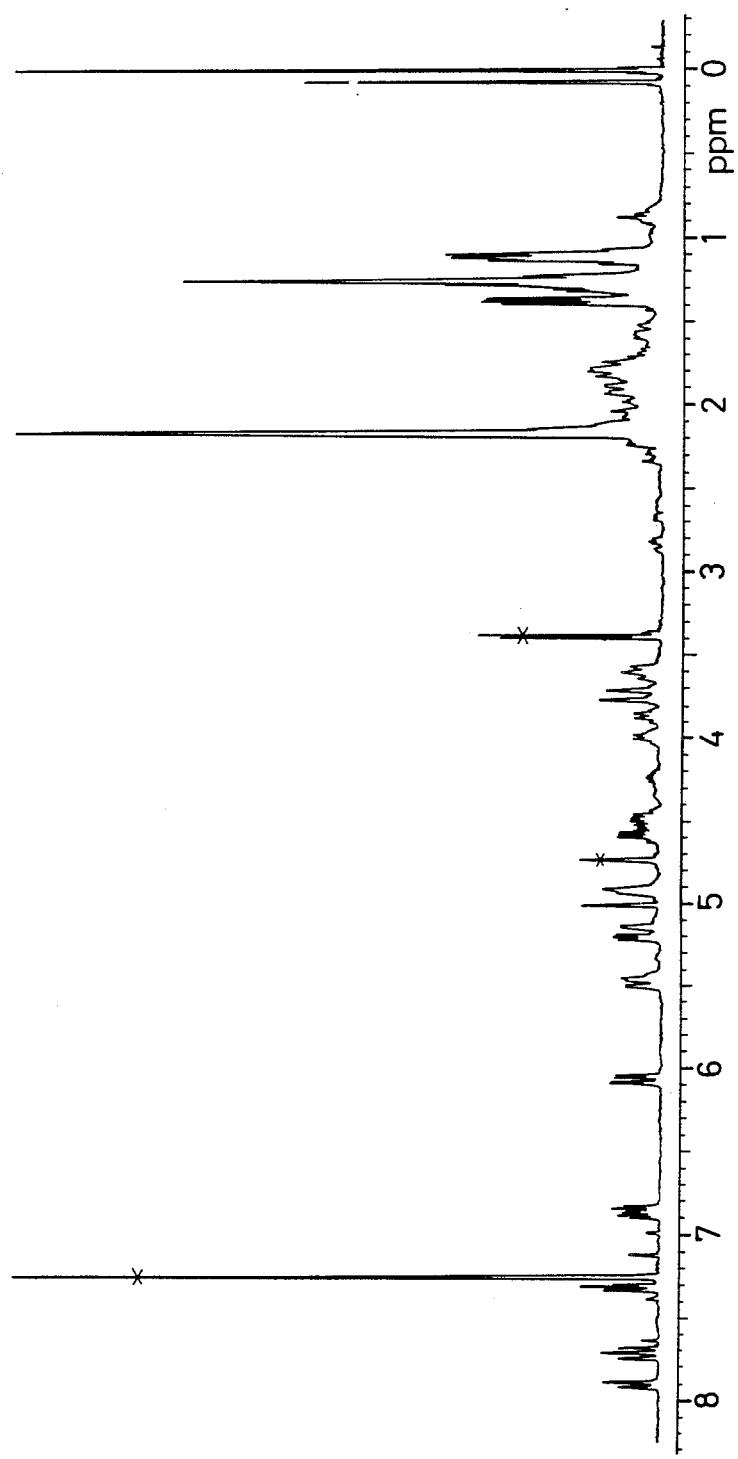

F: $^1$H—NMR Absorption spectrum;  FIG. 5

| (a) 235 (4.55) | 254 (Sh) | 295 (3.79) | 495 (4.04) |
|---|---|---|---|
| (b) 235 (4.55) | 255 (Sh) | 295 (3.79) | 495 (4.04) |
| (c) 243 (4.49) | — | 280 (Sh, 382) | 580, 610 (3.95) |

$C_{60}H_{80}N_2O_{20}$, MW calc. 1148

Figure 6:
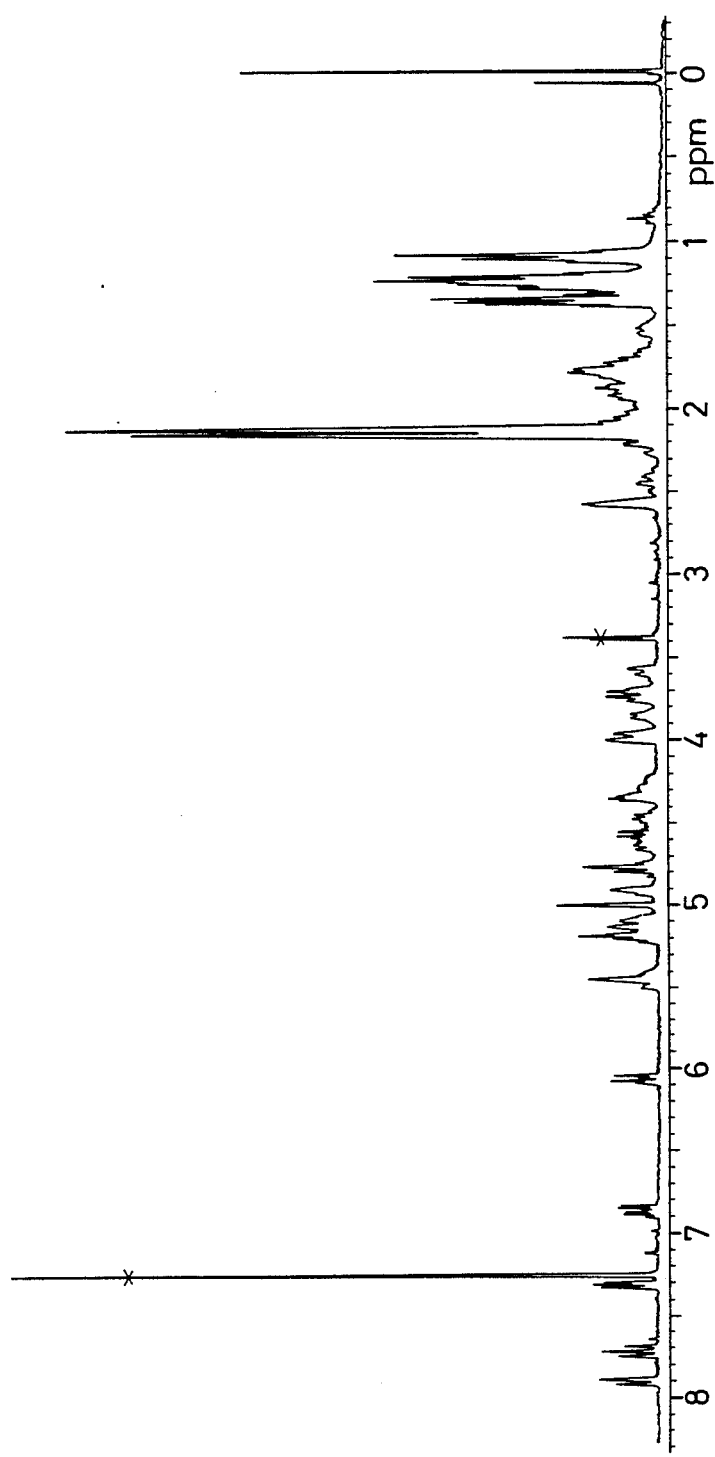

D: $^1$H—NMR Absorption spectrum;  FIG. 6

| (a) 235 (4.62) | 255 (Sh) | 295 (3.82) | 495 (3.17) |
|---|---|---|---|
| (b) 236 (4.75) | 253 (Sh) | 293 (4.0) | 495 (3.30) |
| (c) 242 (4.64) | — | 298 (3.88) | 555 (3.09) |

$C_{60}H_{80}N_2O_{21}$, MW calc. 1164 (confirmed by FAB-MS)

Figure 7:
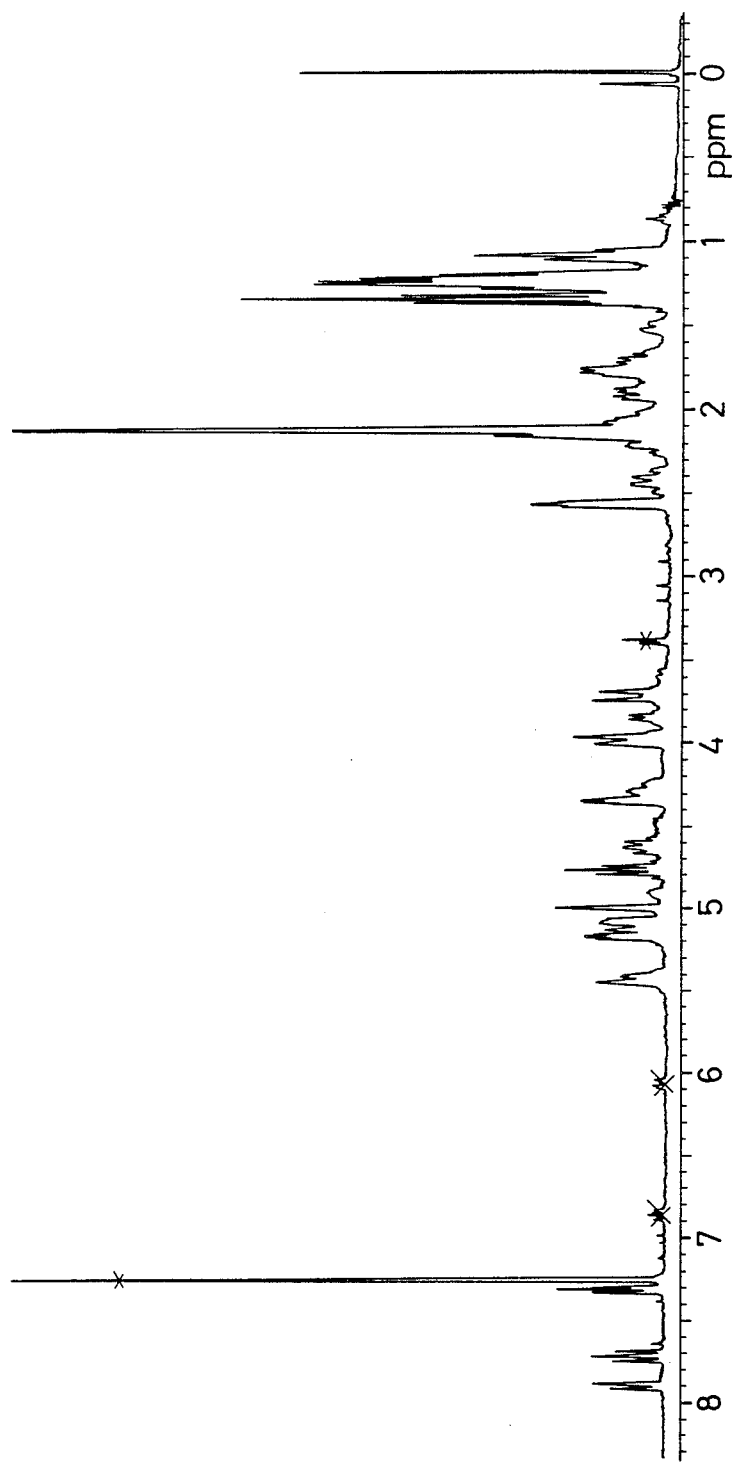

C: $^1$H—NMR Absorption spectrum:  FIG. 7

| (a) 234 (4.68) | 253 (Sh) | 295 (3.85) | 495 (4.11) |
|---|---|---|---|
| (b) 234 (4.68) | 253 (Sh) | 295 (3.92) | 495 (4.18) |
| (c) 244 (4.69) | — | 290 (Sh, 3.85) | 580, 610 (4.18) |

$C_{60}H_{80}N_2O_{22}$, MW calc. 1180 (confirmed by FAB-MS)

Figure 8:
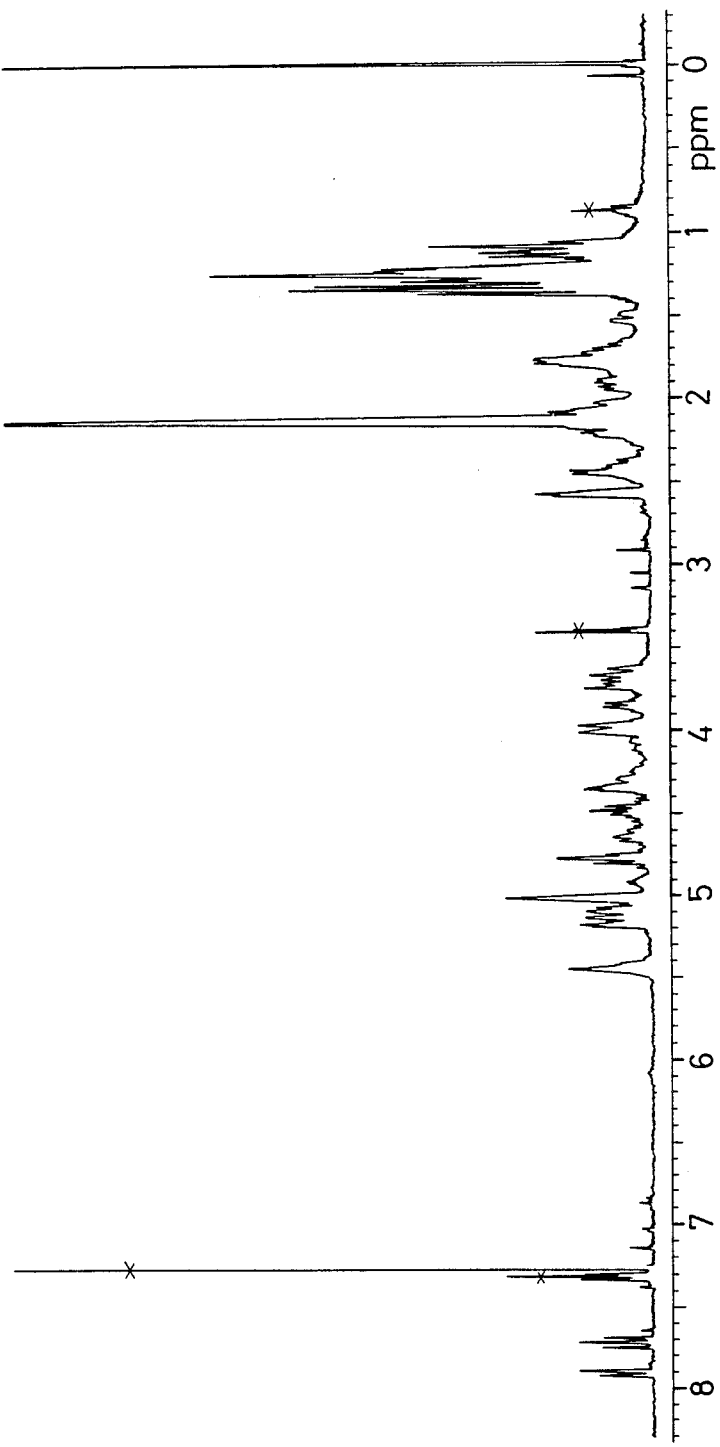

G + I: $^1$H—NMR Absorption spectrum:  FIG. 8

| (a) 237 (4.61) | 256 (Sh) | 300 (3.9) | 495 (4.13) |
|---|---|---|---|
| (b) 236 (4.61) | 255 (Sh) | 295 (3.9) | 495 (4.13) |
| (c) 242 (4.6) | — | 300 (3.9) | 570 (4.1) |

$C_{60}H_{82}N_2O_{22}$ MW calc. 1182 (confirmed by FAB-MS)

The isolated product is a probably a 1:1 mixture of the two structurally isomeric components G and I. This emerges from the $^1$H-NMR spectrum, degradation experiments (hydrogenolysis) and determination of the individual sugar units after total hydrolysis.

EXAMPLE 10

Fractionation of a crude mixture of cytorhodins by partition between toluene and methanol-water.

A fast and simple fractionation of a crude mixture of cytorhodins was performed by partition between toluene and methanol-water 1:1 leading to a less polar fraction (complex I) and a more polar fraction (complex II).

83 g of a crude mixture of cytorhodins, obtained by extraction of the mycelium, were dissolved in 500 ml of methanol-water 1:1 and the solution extracted 5 times with 500 ml of toluene. The combined toluene layers yielded after evaporation in vacuo 32 g of a mixture mainly consisting of less polar cytorhodins (esp. F,D,C,P,V, "X"), whereas the methanol-water phase yielded 47 g of a mixture mainly consisting of more polar cytorhodins (esp. B,H,A,M and "Y").

These two enriched products avarably served as starting materials for further separation and isolation of the individual cytorhodins by column chromatography or droplet.counter-current-chromatography (DCCC) or by a combination of these two procedures, respectively.

EXAMPLE 11

Enrichment of cytorhodins A and N+O by chromatography on a specially modified silica gel.

10 g of a crude mixture of polar cytorhodins (complex II) obtained by partition between toluene and methanol-water were dissolved in 30 ml of the solvent mixture $CHCl_3$/water/methanol 130:40:40 and applied to a glass column (5.5×95 cm) filled with 870 g of a specially modified 31μ silica gel (Grace), and chromatographed with the above mixture as mobile phase. Specially modified silica gel used here was prepared as follows: washing with 2N HCl to get rid of metal ions, neutral washing with water and treating the aqueous slurry with 5N-NaOH up to a pH-value of 7.6.

The water layer was decanted and the basic silica gel was washed with deionized water and finally with a small portion of methanol, then dried 20 at 130° C., sieved and filled into the column as slurry with the above mentioned mobile phase.

The chromatography was carried out at a flow rate of about 100 ml/h, first with 5.5 l of the above mentioned mobile phase then followed by elution with 5.3 l of the mixture of $CHCl_3$/water/methanol 130:40:50. The elute was collected in 15 ml fractions which were combined after checking by TLC, and evaporated in vacuo. After a fore-run of 2 l the following were obtained:

| Fraction | l | g | Compounds |
| --- | --- | --- | --- |
| 1-52 | 0,75 | 0,63 | mixture of unpolar compounds (among others C and D) |
| 53-343 | 4,1 | 2,64 | mixture of compounds of intermediate polarity (e.g. V, G + I, B) |
| 344-400 | 0,9 | 1,7 | mixture of polar compounds (e.g. B, A) |
| 401-430 | 0,3 | 0,56 | mainly A (about 40%) and N + O (about 35%) |
| 431-560 | 1,1 | 1,3 | mixture of very polar compounds (among others A, N + O, W) |

Washing with 1 l of methanol supplied an additional fraction with a mixture of polar to very polar compounds.

EXAMPLE 12

Separation of an enriched mixture of polar cytorhodins by droplet counter current chromatography (DCCC).

5 g of a mixture of enriched polar cytorhodins-methanol-water phase of partitions as described in example 10—were further separated by droplet-counter-current-chromatography (DCCC) using a DCC-Chromatography 670 (Büchi) The sample was dissolved in 20 ml of the lower layer of the heterogenous equilibrated mixture $CHCl_3$/water/methanol/n-propanol 45:90:120:5, 1% 96% strength acetic acid added, and was pumped into the chromatograph. About 3 l of the lower layer were pumped through the system of 288 glas tubes (ID 2.7 nm) in 3 day at a flow rate of 40 ml how and at a pressure of 5–10 bar. The system had been filled before with the upper layer of the above mentioned mixture as the stationary phase ("descending mode). The outflowing mobile phase was collected in 10 ml fractions which were combined after checking by TLC and analytical HPLC and evaporated in vacuo. The following was obtained:

| Fraction | mg | Compounds |
| --- | --- | --- |
| fore run | 800 (oily) | mixture, only slightly different from starting material |
| 1-21 | 660 | mixture of V,L,B |
| 22-27 | 450 | B and some less polar compounds (V,L) |
| 28-33 | 500 | B and non identified less polar compounds |
| 34-55 | 230 | A, M and L |
| 56-63 | 200 | A, M |
| 64-75 | 420 | A, M and more polar components |
| 76-100 | 1300 | fraction "Y" (mainly N + O and W) |

EXAMPLE 13

Isolation of cytorhodin A and N+O from an enriched mixture by "reversed phase" preparative high pressure liquid chromatography (HPLC)

50 mg of a mixture containing about 40% cytorhodin A and about 35% N+O were dissolved in 1.5 ml of the mobile phase $CHCl_3$/methanol/10% aqueous ammoniumacetate 150:1050:375 and applied to a 1.6×25 cm steel column packed with about 30 g of 10μ LiChrosorb ® RP-18 (Merck). Chromatography was carried out under pressure at a flow rate of 2 ml/min and was followed with a spectrophotometer at a wavelength of 490 nm, 4 ml fractions being collected and combined after checking by analytical HPLC.

Analytical HPLC was performed on a 4.6×250 mm HPLC steel column packed with 10μ LiChrosorb ® RP-18 (Merck). For work up the combined fractions were diluted by addition of half the colume of water and $CHCl_3$ until separation of the phases. The lower layer was separated and washed with water, dried over $Na_2SO_4$ and evaporated in vacuo. The pure individual compounds were again purified from traces of grease, metal ions etc. by the procedure described in example 7. Finally the following data were obtained:

| Fraction | mg | Compound | RF in System C |
| --- | --- | --- | --- |
| 15-17 | ca. 5 | enriched Cytorhodin M | (crude) 0.41 |
| 26-30 | 22,5 | enriched Cytorhodin N + O | 0.30 |

| | | -continued | | |
|---|---|---|---|---|
| 35–40 | 10,4 | enriched Cytorhodin A | | 0.41 |

System C: CHCl$_3$/methanol/99% strength acetic acid/water

Figure 9:
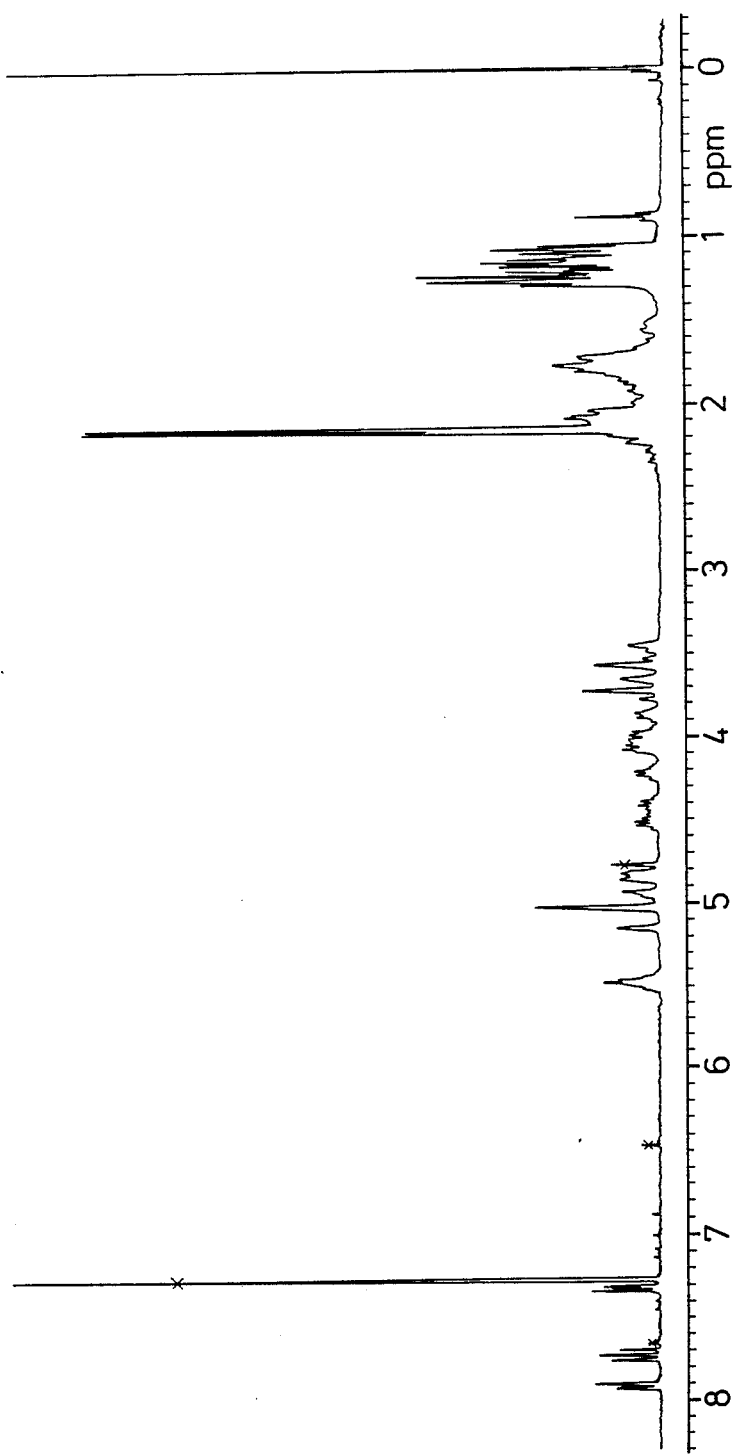

| N + O: $^1$H—NMR | | | FIG. 9 | |
|---|---|---|---|---|
| Absorp- | (a) 235 (4.56) | 253 (Sh) | 293 (3,67) | 495 (4.04) |
| tion- | (b) 234 (4.59) | 253 (Sh) | 293 (3.68) | 495 (4.15) |
| Spectrum | (c) 240 (4.51) | — | 283 (3.81) | 575 (4.0) |

C$_{60}$H$_{88}$N$_2$O$_{21}$, M calc.; 1172 (conformed by FAB-MS)

The isolated product is mixture (probably 1:1) of the two structurally isomeric components N and O. This emerges from the $^1$H-NMR Spectra, degradation experiments (hydrogenolysis) and determination of the individual sugar units and the aglycon after acidic total hydrolysis. Component Cytorhodin O is known from the literature (H. Brockmann and H. Greve, Tetrahedron Letters 831–834 (1975)).

EXAMPLE 14

Isolation of the single componente cytorhodin P by pressure liquid chromatography and preparative thin layer chromatography 6 g of a crude mixture of cytorhodins, obtained by extraction out of the solution from the culture filtrate as described in Diagram I, was chromatographed on 620 g 31μ silica gel (Grace) in two radially compressed certridges (Water, Prep LC/System 500 ®) using the mixture of CHCl$_3$/methanol/96% strength acetic acid/water 80:10:10:2. The sample was dissolved in 50 ml of the mobile phase, applied to the equilibrated columns, and at a flow rate of 35 ml/min fractions of each 23 ml were collected and assessed by HPLC. Fractions 41–56 yielded 220 mg Cytorhodin P of 88% purity (RF 0.42 in System A). 40 mg of this product were further purified by preparative thin-layer chromatography (TLC sheets, silica gel 60 F 254, precoated, Merck) with System A.

Elution of the main band was carried out by extraction with CHCl$_3$/methanol 1:1. The filtered extract was neutralized with an aqueous solution of Na$_2$HPO$_4$ and diluted with water until separation of the phases. The separated CHCl$_3$ layer was washed with water, dried over anhydrous Na$_2$SO$_4$ and evaporated (in vacuo). The residue was dissolved in a little CHCl$_3$ and precipitated with petroleum ether. 15 mg of pure dried cytorhodin P were obtained.

Figure 10:
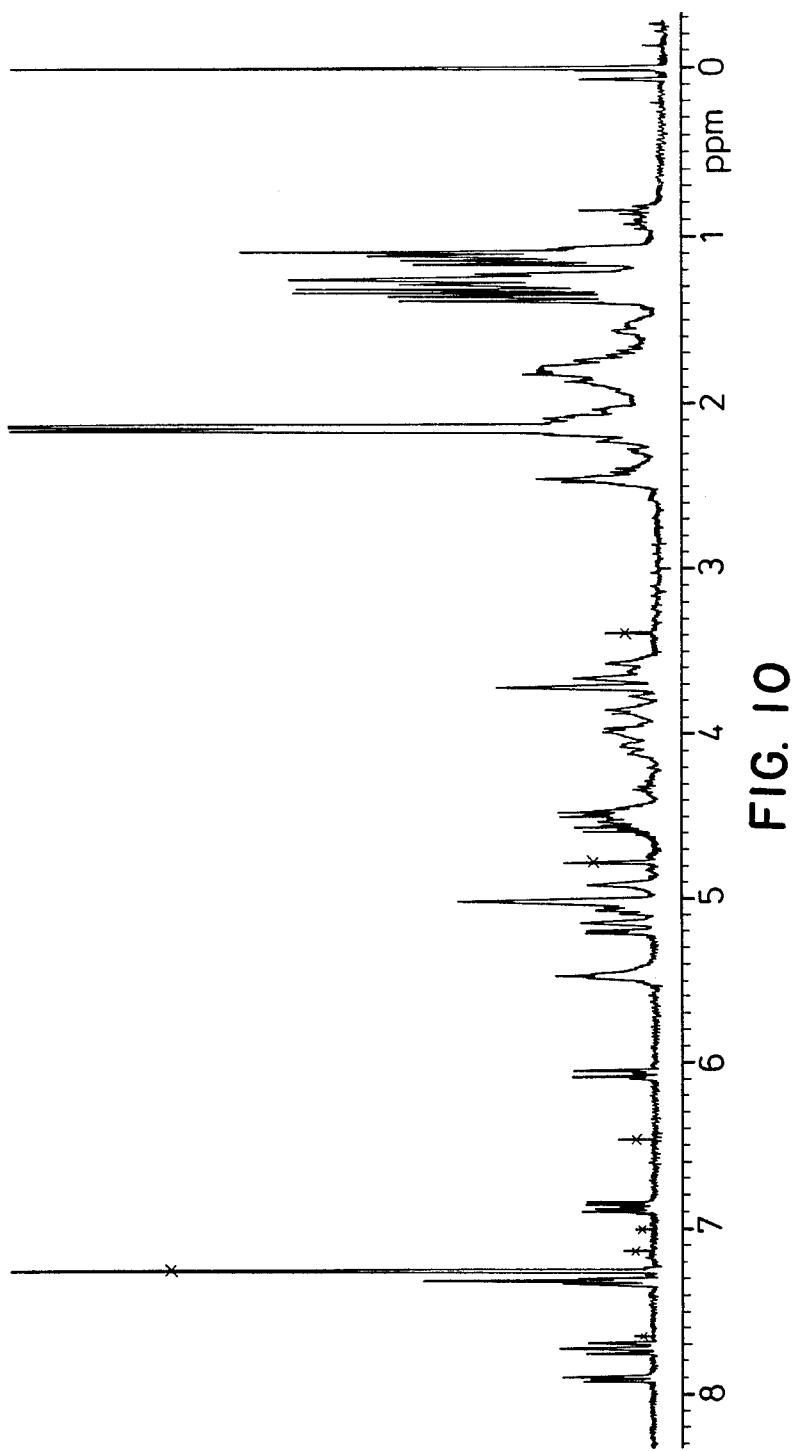
Figure 11:
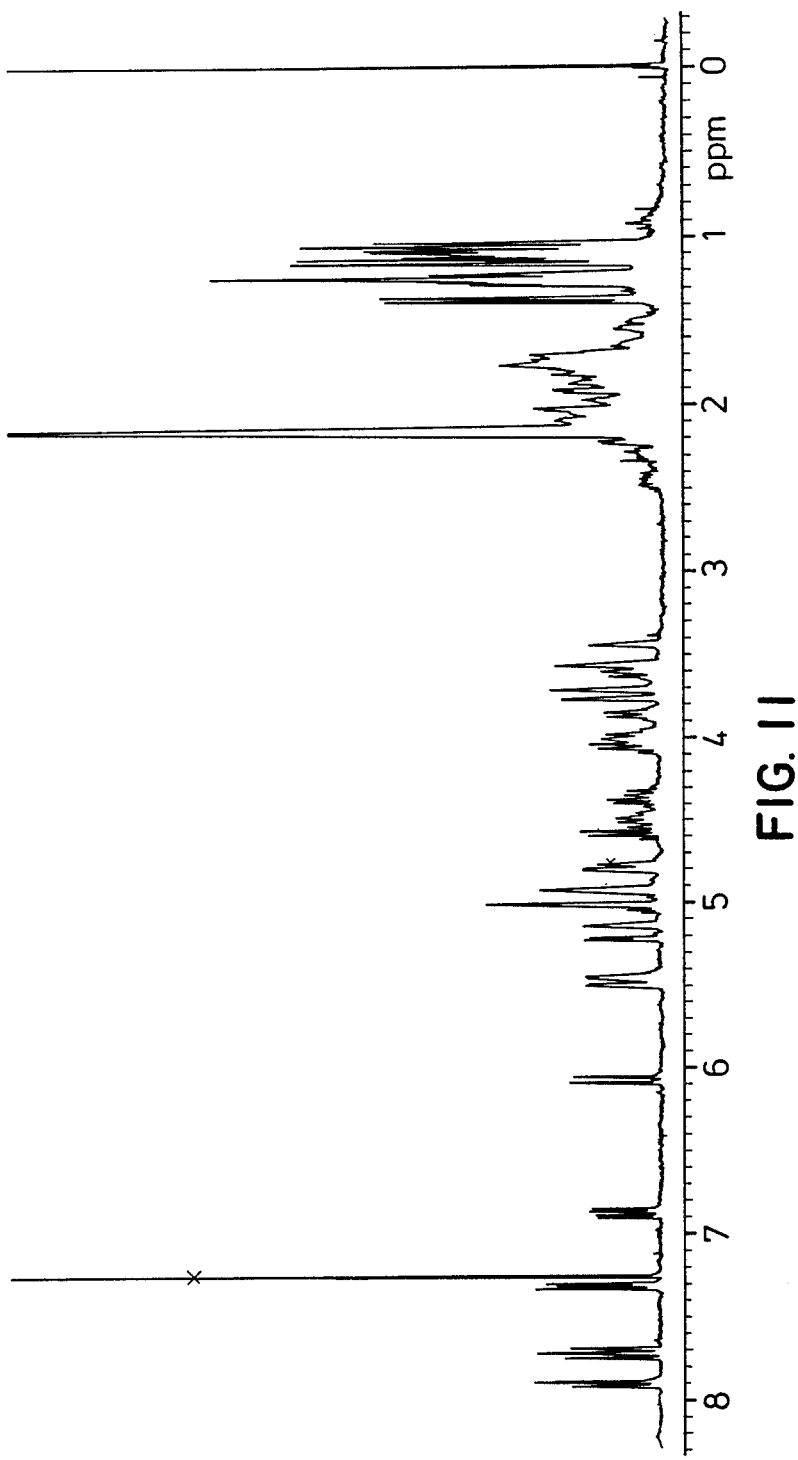
Figure 12:
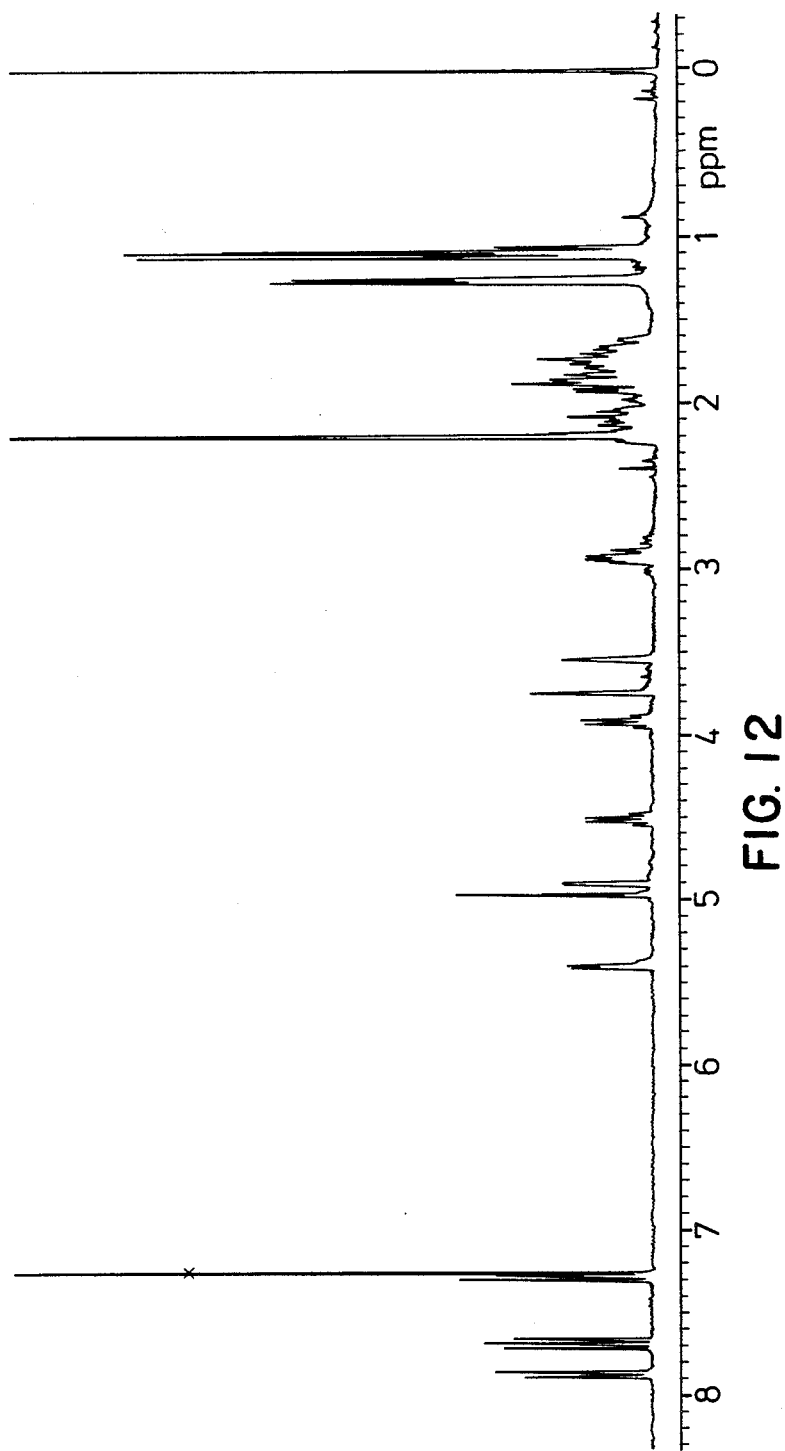
Figure 13:
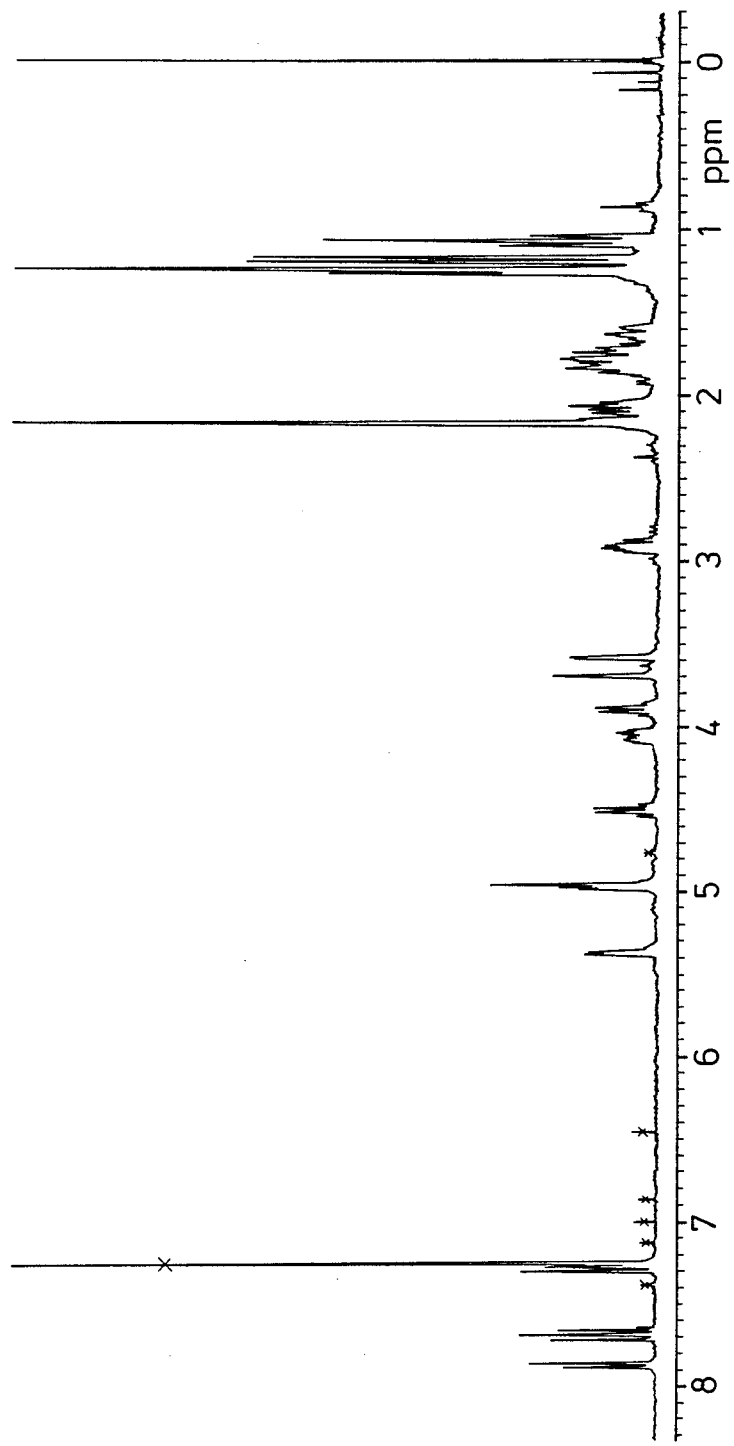

| P: $^1$H—NMR | | | FIG. 10 | |
|---|---|---|---|---|
| Absorption | (a) 235 (4.63) | 254 (Sh 4.33) | 253 (3.90) | 494 (4.13) |
| Spectrum | (b) 235 (4.60) | 254 (Sh 4.31) | 293 (3.85) | 494 (4.12) |
| (nm) | (c) 244 (4.33) | — | 570 (3.59) | 620 (3.71) |

C$_{60}$H$_{82}$N$_2$O$_{21}$, MW calc.: 1166 (confirmed by FAB-MS)

EXAMPLE 15

Isolation of cytorhodin V by preparation pressure liquid chromatography and thin layer chromatography.

7 g of a crude mixture of cytorhodins, obtained by extraction out of the solution from the culture filtrate as described in Diagram I, was chromatographed on 620 g 31μ silica gel (Grace) in two radially compressed cartridges (Waters, PrepLC/System 500 ®) using the mixture CHCl$_3$/methanol 96% strength acetic acid/water 80:10:10:2. The sample was dissolved in 65 ml of the mobile phase, applied to the equilibrated columns, and at a flow rate of 25 ml/min fractions of 23 ml were collected assessed by HPLC. Fractions 29–34 yielded 195 mg Cytorhodin V of 80% purity (RF 0.38 in System A). 60 mg of this product were further purified by preparative thin-layer chromatography (TLC-sheets, silica gel 60, pre-coated, Merck) with System A. Elution of the resulting main band and isolation of cytorhodin V was performed as described in example 14. 16 mg of pure V were obtained.

| V: $^1$H—NMR | | | FIG.: 11 | |
|---|---|---|---|---|
| Absorp- | (a) 235 (4.72) | 254 (Sh 4.48) | 290 (4.04) | 495 (4.20) |
| tion | (b) 235 (4.73) | 254 (Sh 4.48) | 290 (4.06) | 494 (4.24) |
| Spectrum | (c) 244 (4.61) | 269 (4.63) | — | 570 (4.22) |
| | | | | 601 (4.19) |

C$_{60}$H$_{88}$N$_2$O$_{20}$, M ber. 1152 (confirmed by FAB-MS)

EXAMPLE 16

Isolation of cytorhodin K by column chromatography and preparative thin layer chromatography.

6 g of a crude mixture of cytorhodins obtained by extraction out of the solution from the culture was described in Diagram I were dissolved in 100 ml of water at pH 7.5 and reextracted with ethylacetate. The organic layer was evaporated (in vacuo) the resulting residue was dissolved in 15 ml of CHCl$_3$ and the solution was treated with ten times the volume of petrolether. The precipitate was separated by centrifugation washed with petrol ether and dried in vacuo yielding 3.6 g 450 mg of this product were chromatographed on 80 g of silica gel 60, 15-4,0μ (Merck) with a mixture of CHCl$_3$/methanol/96% strength acetic acid/water 80:10:10:2. The sample was dissolved in a small amount of the above mentioned mobile phase and was applied to the equilibrated glass column. After a forerun of 210 ml fractions of 5 ml were collected. The combined fractions 64–76 contained 15 mg cytorhodin K (purity 62% assessed by HPLC).

The product was further purified by preparative TLC (Merck, TLC sheets silica gel 60, precoated) with System A (see examples 14 and 15) leading to 3.6 mg of pure cytorhodin K. K: identified by $^1$H-NMR as rhodomycin Y (H. Brockmann and T. Wachneldt, Naturwiss. 48, 717 (1961) see also: E. Biedermann and H. Bräuniger, Pharmazic 27, 782–789 (1972).

C$_{40}$H$_{53}$N$_1$O$_{14}$, MW calc. 771

EXAMPLE 17

Isolation of cytorhodin L by column liquid chromatography and preparative thin layer chromatography.

6 g of crude mixture of cytorhodins, obtained by extraction out of the solution from the culture as described in Diagram I, was chromatographed on 800 g of 15–40μ silica gel 60 (Merck). A gradient mixture of the solvents CHCl$_3$, methanol, 96% strength acetic acid and water was used for elution, starting with 1.65 l of the ratio of 80:10:10:2 (System A) followed by 4 l of the same mixture varied by addition of 0.01% of heptanesulfonic acid, then 3.6 l of 70:20:10:1 and finally 2.8 l of 50:50:5:2 with 0.01% heptane sulfonic acid. The sample was dissolved in 50 ml of the first mentioned mixture and applied to the equilibrated column. After a forerun of 1.65 l fractions of 25 ml were collected and assessed by TLC and HPLC. Fractions 161–225 yielded 1.1 g of a mixture containing 24% of component L. This material was again separated by chromatography on 160 g of 15–40μ silica gel 60 (Merck) with the mixture CHCl$_3$/methanol/96% strength acetic acid/water 80:10:10:2 The sample was dissolved in the mobile phase and applied to the equilibrated column and after a forerun of 700 ml fractions of 10 ml were collected Fractions 91–102 (31 mg) containing 64% L and 103–118 (44 mg) containing 68% L were combin-d and 50 mg of the resulting product were further separated by preparative TLC (Merck, TLC sheets silica gel 60, precoated, with system A, as in examples 14 and 15). 18 mg of cytorhodin L of a purity of 74%/HPLC) were obtained which after final preparative TLC yielded 14 mg of pure Cytorhodin L

| L: $^1$H—NMR | | | FIG.: 12 | |
|---|---|---|---|---|
| Absorption-Spectrum (nm) | (a) 235 (4.59) | 253 (Sh) | 295 (3.86) | 4.95 (4.1) |
| | (b) 235 (4.6) | 255 (Sh) | 295 (3.91) | 495 (4.13) |
| | (c) 244 (4.61) | — | 303 (3.87) | 570 (4.1) |
| | | | | 610 (4.15) |
| $C_{34}H_{43}N_1O_{11}$, MW calc. 641 | | | | |

EXAMPLE 18

Isolation of cytorhodin M by preparative "reversed phase" high pressure liquid chromatography 50 mg of a batch of Cytorhodin A from preparative HPLC on silical gel, which showed pronounced tailing in analytical HPLC, was dissolved in 2 ml of the mixture CHCl$_3$/methanol-10% aqueous ammonium-acetate 150:1050:375 and applied on a 1.6×25 cm stell column packed with about 35 g of 10μ LiChrosorb® RP-18 (Merck). Elution was carried out under pressure at a flow rate of 2 ml/min and was followed with a flow spectrophotometer at a wavelength of 490 nm, 4 ml fractions being collected and combined after checking by analytical HPLC (example 13):

| Fraction | | Compounds | RF-System A |
|---|---|---|---|
| 18–20 | 10 mg | Cytorhodin M | 0.27 |
| 49–55 | 25 mg | Cytorhodin A | 0.27 |

Cytorhodin M could not be differentiated from Cytorhodin A by TLC or HPLC on Silica gel with the mobile phase system A. Separation was achieved by TLC with the mixture CHCl$_3$/methanol/99% strength acetic acid 75:15:10:2 (System C) on pre-coated TLC plates or sheets silica gel Si 60 (Merck): RF 0.41 (A) and 0.37 (M)

| M: $^1$H—NMR | | | FIG.: 13 | |
|---|---|---|---|---|
| Absorption-Spectrum (nm) | (a) 235 (4.50) | 253 (Sh) | 295 (3.83) | 495 (4.10) |
| | (b) 235 (4.58) | 256 (Sh) | 296 (3.89) | 496 (4.15) |
| | (c) 244 (4.59) | — | 305 (3.87) | 610 (4.10) |
| $C_{34}H_{43}N_1O_{12}$, MW calc.: 657 (conformed by FAB-MS) | | | | |

EXAMPLE 19

Isolation of cytorhodin W by preparative high pressure liquid chromatography (HPLC)

80 mg of the polar fraction "Y" was dissolved in 2 ml of the mobile phase CHCl$_3$/methanol/96% strength acetic acid/triethylamine 80:10:10:0.01 saturated with water and applied to a 3.2×25 cm steel column packed with 110 g 7μ Lichrosorb® Si60 (Merck) and chromatographed under pressure at a flow rate of 8 ml/min. Fractions of 4 ml were collected and checked by analytical HPLC and combined and worked up in the usual manner. Besides some other not identified components 1.5 mg of compound Cytorhodin W were isolated showing RF 0.23 in system C on the usual pre-coated TLC plates silica gel 60 (Merck).

| W: | | | | |
|---|---|---|---|---|
| Absorption-Spectrum | (a) 235 (4.53) | 253 (Sh) | 293 (3.64) | 495 (4.01) |
| | (b) 235 (4.57) | 253 (Sh) | 293 (3.65) | 495 (4.13) |
| | (c) 241 (4.49) | — | 282 (3.78) | 575 (3.81) |
| | | | | 610 (3.96) |
| $C_{60}H_{88}N_2O_{22}$, MW calc. 1184 | | | | |

The components in the preceding examples were identified using the conditions of measurement described below:

The proton resonance spectre ($^1$H-NMR spectra) were recorded at 270 MHz using an HX-270 BRUKER Fourier transform nuclear magnetic resonance spectrometer. The concentrations were 2–4 mg/0.5 ml of 99.8%. CDCl$_3$; immediately after preparation, the solutions were shaken with 0.1 ml of 5% Na$_2$CO$_3$ in 99.5% D$_2$O.

The signals identified by an asterisk in the figures derive from low molecular weight contamination, in the $10^{-3}$ range, and from residual solvent.

The mass spectra were recorded using an MS-902 S, AEI, mass spectrometer using an FAB (fast atom bombardment) ion source. The substances were inserted in a matrix of thioglycerol into the ion source, ammonium chloride sometimes being added.

The absorption spectra were recorded in the range 200–700 nm in:
(a) water/methanol 1:9
(b) 10% 1N HCl in methanol
(c) 10% 1N NaOH in methanol The concentration of the substances was 10–30 mg/l; the absorption maxima in nm and the molar extinction coefficients (log ε) are reported.

Determination of the cytotoxic activity

The cytostatic activity of the compounds described in this text was determined on L1210 mouse leukemia cells. Specifically, the following test systems were used:
(a) Proliferation assay In this method, the extent to which the cells can incorporate radioactive DNA precursors (for example $^{14}$C-labeled thymidine) in vitro is determined after incubation of the cells with various concentrations of the test substance. Untreated L1210 cells are subjected to the same test conditions and serve as the control. The method is briefly described below:

L1210 cells in the exponential phase of growth ($5 \times 10^3$/ml in RPMI 1640) are incubated in a microtiter plate with various concentrations of the test substance for 72 hours (37° C., 5% CO$_2$, 95% relative humidity). The controls comprise cells which are merely incubated with fresh medium. All determinations are carried out in quadruplicate. After 65 hours, 50 μl of $^{14}$C-thymidine (1.5 μCi/ml) are added in order to radiolabel the DNA in the cells. After incubation for 7 hours, the cells are filtered off with suction, the DNA is precipitated with 5% strength trichloroacetic acid and is then washed consecutively with water and methanol.

After drying at 50° C. and addition of 5 ml of scintillation liquid, the radioactivity incorporated in the DNA is measured.

The results are reported as the ratio of the scintillation count after incubation with the test substance as a percentage of the untreated control. The dose-activity curve is derived from the figures thus measured, and the IC$_{50}$, i.e. the concentration which decreases the incorporation of radioactive thymidine by 50% compared with the control under the test conditions, is determined graphically. The IC$_{50}$ figures for the compounds described in this text are summarized and compared with adriamycin (ADM) in Table 1.

(b) Formation of colonies of L1210 leukemia cells in soft agar

This method is used to detect an effect of the test substance on the growth characteristics of the cells over several generations (with the cell cycle period being 10–12 hours, about 14 consecutive generations are observed in the 7-day test period).

In this test, substances having cytostatic effects bring about a reduction in the number of colonies found compared with an untreated control. Specifically, the test is carried out as follows:

500 leukemia cells per plate are incubated with various concentrations of the test substance at 37° C. for 1 hour. The cells are then washed twice with McCoy 5a medium and, after addition of 0.3% agar, are finally poured into Petri dishes. Controls are merely incubated with fresh medium. In some cases, in place of incubation for 1 hour, various concentrations of the test substance are mixed into the upper agar layer in order thus to achieve continuous exposure of the cells throughout the incubation time. After the agar has solidified, the plates are incubated in an incubator at 37° C. for 7 days (5% $CO_2$, 95% relative humidity). Then the number of resulting colonies having a diameter of 60$\mu$ is counted. The results are reported as the number of colonies in the treated agar plates as a percentage of the untreated control. The IC$_{50}$ is determined from the dose-activity curve thus obtained and serves as a measure of the action of the substance. The results for the compounds described in this text are summarized and compared with adriamycin in Table 1.

TABLE 1

| | Proliferation test IC$_{50}$ ($\mu$g/ml) | Colony formation test IC$_{50}$ ($\mu$g/ml) | |
|---|---|---|---|
| | | 7 days incubation | 1 hour incubation |
| ADM | $6.0 \times 10^{-3}$ | $2.2 \times 10^{-2}$ | $4.4 \times 10^{-2}$ |
| Cytorhodin B | $2.8 \times 10^{-3}$ | $3.4 \times 10^{-3}$ | $1.2 \times 10^{-3}$ |
| " A | $1.1 \times 10^{-3}$ | $3.0 \times 10^{-3}$ | $1.3 \times 10^{-3}$ |
| " G + I | $2.8 \times 10^{-4}$ | $< 10^{-4}$ | $2 \times 10^{-3}$ |
| " C | $5.5 \times 10^{-4}$ | $1.5 \times 10^{-4}$ | $3.4 \times 10^{-3}$ |
| " D | $2.8 \times 10^{-4}$ | $3.7 \times 10^{-3}$ | $2.8 \times 10^{-3}$ |
| " F | $2.4 \times 10^{-3}$ | $2.8 \times 10^{-2}$ | $4.2 \times 10^{-2}$ |
| " J | $4.4$ | — | —(*) |
| E | $2.5 \times 10^{-2}$ | $1.4 \times 10^{-3}$ | $2.8 \times 10^{-2}$ |
| P | $2.6 \times 10^{-3}$ | $3.2 \times 10^{-4}$ | $2.8 \times 10^{-3}$ |
| V | $2.9 \times 10^{-3}$ | $2.7 \times 10^{-4}$ | $2 \times 10^{-3}$ |
| K | $3.7 \times 10^{-3}$ | $3 \times 10^{-3}$ | $3.1 \times 10^{-2}$ |
| L | $3 \times 10^{-1}$ | $2.1 \times 10^{-1}$ | $1.75$ |
| M | $2.8 \times 10^{-1}$ | $1.6 \times 10^{-1}$ | $3.9 \times 10^{-1}$ |
| N + O | $5 \times 10^{-3}$ | $2.5 \times 10^{-3}$ | $4.5 \times 10^{-2}$ |

(*)not tested

TABLE 2

Characteristics of Streptomyces Y-11472

(a) Morphology

Section Spirales. Mature spore chains moderately long with 10 to 50 or more spores per chain. This morphology is seen on yeast-malt agar, oatmeal agar, salts-starch agar and glycerol-asparagine agar.

(b) Cultural Characteristics on

| Medium | Growth | Reverse | Aerial mycelium | Soluble Pigment |
|---|---|---|---|---|
| 1. Yeast malt agar | good, wrinkled dry | reddish purple | good, cottonly, yellowish pink | brownish pink |
| 2. Oatmeal agar | good, flat, dry | pale pink | good, powdery, yellowish pink | pale pink |
| 3. Inorganic salts-starch agar | moderate, flat dry | colourless to pale yellowish pink | good, cottony, light yellowish pink | pale yellowish pink |
| 4. Glycerol-asparagine agar | moderate, wrinkled dry | reddish purple | moderate, powdery, grayish pink | pale reddish purple |
| 5. Potato glucose agar | good, elevated dry | brown | good, velvety, pale yellowish white | violet |
| 6. Peptone-yeast iron agar | good, elevated, moist | colourless to pale yellow | none | reddish brown |
| 7. Tyrosine agar | good, raised dry | brown | good, cottony, light grayish pink | reddish brown |
| 8. Czapeck's agar | good, wrinkled dry | purple | moderate, cottony, pale yellowish white | light purple |

(c) Physiological properties

| | |
|---|---|
| 1. Temperature range for growth: | grows on yeast-malt agar in the temperature range 24–40° C., with optimal growth at 30° C. |
| 2. Nitrate reduction: | positive |
| 3. Melanine formation: | " |
| 4. Gelatine utilization: | " |
| 5. Starch hydrolysis: | " |
| 6. Tyrosine hydrolysis: | " |
| 7. Sodium chloride tolerance: | $> 7.0\%$ but $< 10.0\%$ |
| 8. Casein hydrolysis: | positive |
| 9. Gelatine liquefaction: | " |
| 10. Urease production: | " |
| 11. Streptomycin inhibition: | inhibition at 12.5 $\mu$g per ml |
| 12. pH sensitivity: | |

The substrate mycelium and the diffusible pigment are pH sensitive. Violet (purplish red) under alkaline conditions and red (pink) under acid conditions.

(d) Utilization of carbon

D-glucose, L-arabinose, sucrose, D-xylose, I-inositol, D-mannitol, D-fructose, rhamnose, raffinose, galactose, salicin, maltose, cellobiose, ribose, Na glutamate and sorbitol are used for growth. It is unclear whether cellulose is utilized.

We claim:

1. A compound of the formula I

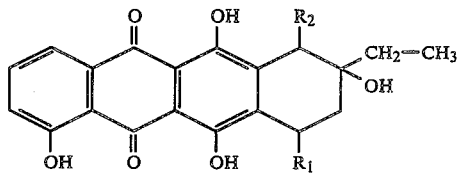

wherein $R_1$ represents the radical $OR_3$, and $R_2$ represents the radical $OR_4$, $R_3$ and $R_4$ being identical or different and representing sugar combinations of the following composition: Roa—dF—Rod, Roa—dF—Cin A, Roa—dF=Cin B, Roa—Rod—Rod, Roa—Rod—Cin A, Roa—Rod—Acu, Rod—Rod—Rod, Roa—dF—Acu, Roa—Rod or Roa—dF, except that when $R_4$ is Roa—Rod—Rod or Roa—dF, $R_3$ cannot be Roa—Rod or Roa—dF—Rod, in which Roa: represents rhodosamine,
dF: represents deoxyfucose,
Rod: represents rhodinose,
Acu: represents aculose,
Cin A: represents cinerulose A and
Cin B: represents cinerulose B, and dF=Cin B denotes that the two sugar units are linked, or a physiologically acceptable acid addition salt thereof.

2. A compound as claimed in claim 1, wherein $R_3$ represents the sugar combination Roa—Rod—Acu and $R_4$ represents the sugar combination Roa—Rod—Acu, and its physiologically acceptable acid addition salts.

3. A compound as claimed in claim 1, wherein $R_3$ represents the sugar combination Roa—dF—Cin A, and $R_4$ represents the sugar combination Roa—Rod—Rod, and its physiologically acceptable acid addition salts.

4. A compound as claimed in claim 1, wherein $R_3$ and $R_4$ represent the sugar combination Roa—Rod—Rod, and its physiologically acceptable acid addition salts.

5. A compound as claimed in claim 1, wherein $R_3$ represents the sugar combination Roa—dF=Cin B, and $R_4$ represents the sugar combination Roa—dF—Cin A, and its physiologically acceptable acid addition salts.

6. A compound as claimed in claim 1, wherein $R_3$ represents the sugar combination Roa—dF—Cin A and $R_4$ represents the sugar combination Roa—Rod—Acu, and its physiologically acceptable acid addition salts.

7. A compound as claimed in claim 1, wherein $R_3$ represents the sugar combination Roa—Rod—Acu and $R_4$ represents the sugar combination Roa—Rod—Rod, and its physiologically acceptable acid addition salts.

8. A compound as claimed in claim 1, wherein $R_3$ represents the sugar combination Roa—Rod—Rod and $R_4$ represents the sugar combination Roa—dF—Rod, and its physiologically acceptable acid addition salts.

9. A compound as claimed in claim 1, wherein $R_3$ and $R_4$ represent each the sugar combination Roa—dF—Rod, and its physiologically acceptable acid addition salts.

10. A pharmaceutical composition for use as an antibacterial agent comprising a therapeutically effective amount of the compound according to claim 1 or its physiologically acceptable salts in association with a pharmaceutically acceptable carrier.

11. A method for treating bacterial infection which comprises the administration to a host in need of such treatment of a therapeutically effective amount of the compound according to claim 1.

12. A pharmaceutical composition for use as a cytostatic agent comprising a therapeutically effective amount of the compound according to claim 1 or its physiologically acceptable salts in association with a pharmaceutically acceptable carrier.

* * * * *